United States Patent
Michaelis

(10) Patent No.: US 9,823,233 B2
(45) Date of Patent: Nov. 21, 2017

(54) DETERMINING THE KNOCK RATING OF LIQUID SPARK-IGNITION ENGINE FUELS

(71) Applicant: Chad Alan Michaelis, Aledo, TX (US)

(72) Inventor: Chad Alan Michaelis, Aledo, TX (US)

(*) Notice: Subject to any disclaimer, the term of this patent is extended or adjusted under 35 U.S.C. 154(b) by 503 days.

(21) Appl. No.: 14/522,181

(22) Filed: Oct. 23, 2014

(65) Prior Publication Data

US 2015/0120211 A1    Apr. 30, 2015

Related U.S. Application Data

(60) Provisional application No. 61/895,744, filed on Oct. 25, 2013.

(51) Int. Cl.
*G01N 33/22* (2006.01)
*G01N 33/28* (2006.01)

(52) U.S. Cl.
CPC ......... *G01N 33/22* (2013.01); *G01N 33/2829* (2013.01)

(58) Field of Classification Search
CPC ... G01N 33/02; G01N 33/227; G01N 33/2829
See application file for complete search history.

(56) References Cited

U.S. PATENT DOCUMENTS

| | | |
|---|---|---|
| 3,456,493 A | 7/1969 | Roddick |
| 4,010,358 A | 3/1977 | Morris |
| 4,254,354 A | 3/1981 | Keem |
| 4,305,013 A | 12/1981 | Baier et al. |
| 4,331,024 A | 5/1982 | Childs et al. |
| 4,379,404 A | 4/1983 | Hamisch et al. |

(Continued)

FOREIGN PATENT DOCUMENTS

| | | |
|---|---|---|
| EP | 0 671 612 B1 | 3/1999 |
| JP | 61-17916 | 1/1986 |
| JP | 8-338781 | 12/1996 |

OTHER PUBLICATIONS

Genchi et al., Knock Resistance Increase Through the Addition of Natural Gas or LPG to Gasoline: An Experimental Study, 2012 SAE International, SAE Technical Paper 2013-24-0100, 8 pp.*

(Continued)

*Primary Examiner* — Toan Le
(74) *Attorney, Agent, or Firm* — Carrington, Coleman, Sloman & Blumenthal, L.L.P.

(57) ABSTRACT

A system and method for determining the octane rating of a fuel from a plurality of measurements at a test engine. The measurements may include a plurality of measurements regarding individual knock events, from which waveform attributes regarding the knock events can be determined and used in the calculation of the octane rating. The measurements may also include one or more environmental measurements, such as temperature, humidity, exhaust oxygen, etc., according to which the octane rating may be normalized or that may otherwise be applied into the calculation of the octane rating. The measurements may also include one or more engine property measurements corresponding to the condition of the test engine, according to which the octane rating may be normalized or that may otherwise be applied into the calculation of the octane rating, and that may be used to advise of maintenance events.

15 Claims, 10 Drawing Sheets

(56) References Cited

U.S. PATENT DOCUMENTS

| | | | |
|---|---|---|---|
| 4,393,688 A | 7/1983 | Johnston et al. | |
| 4,660,410 A | 4/1987 | Asano et al. | |
| 4,976,241 A | 12/1990 | Ishida et al. | |
| 5,633,798 A * | 5/1997 | Kopp | G01N 33/2817 701/104 |
| 5,635,629 A | 6/1997 | Imai et al. | |
| 6,094,984 A | 8/2000 | Asano et al. | |
| 6,398,252 B1 | 6/2002 | Ishikawa et al. | |
| 7,100,426 B2 | 9/2006 | Aoi et al. | |
| 7,444,231 B2 | 10/2008 | Ancimer et al. | |
| 7,529,616 B2 | 5/2009 | Bizub | |

OTHER PUBLICATIONS

International Search Report and Written Opinion of the ISA, PCT International Application PCT/US2014/061993 (dated Feb. 5, 2015).
Cosby, "Knock Sensor Training" (Texas Instruments Incorporated, 2011).
"Engine Knock Sensing Applications", Application Note AN9770.1 (Intersil Americas, Inc., 1999, 2006).
Park et al., "Engine Knock Detection Based on Wavelet Transform", Proceedings of the 8th Russian-Korean International Symposium on Science and Technology (2004), vol. 3, pp. 80-83.
"Standard Test Method for Motor Octane Number of Spark-Ignition Engine Fuel", Designation D2700-12 (ASTM, 2012).
"Delphi Flat Response Knock Sensor" (Delphi, 2008).
EPO, Communication (European Search Report), dated Apr. 19, 2017, pp. 1-10; EP App. 14855389.4.
EPO, Communication (supplementary European Search Report), dated May 9, 2017, pp. 1-4; EP App. 14855389.4.

* cited by examiner

DETERMINING THE KNOCK RATING OF LIQUID SPARK-IGNITION ENGINE FUELS

CROSS-REFERENCE TO RELATED APPLICATIONS

This application claims priority, under 35 U.S.C §119(e), of Provisional Application No. 61/895,744, filed Oct. 25, 2013, incorporated herein by this reference.

STATEMENT REGARDING FEDERALLY SPONSORED RESEARCH OR DEVELOPMENT

Not applicable.

BACKGROUND OF THE INVENTION

This invention is in the field of liquid spark-ignition engine fuel octane testing. More specifically, embodiments of the invention are directed to methods of measuring the octane number of a sample fuel by running that fuel on a test engine, for example an ASTM standard Cooperative Fuels Research (CFR) engine.

Gasoline fuels for use in internal combustion engines are sold according to their octane ratings, with fuels of higher octane ratings priced higher than those with lower octane ratings. As known in the industry, the octane rating (or "octane number") is a measure of the ability of the fuel to resist "detonation" which is the spontaneous combustion of unburned gasoline in the cylinder triggered by the high temperature and pressure resulting from the spark-initiated combustion, but occurring well after that combustion and near the end of the engine cycle. This detonation, which is also referred to as "knock" or "ping" due to its characteristic resonant sound, adds nothing to the power output of the engine, but can cause engine damage over time. In a practical sense, a higher octane fuel will resist detonation as compared with lower octane fuel, under the same conditions of temperature and pressure.

As known in the industry, the conventional method for measuring the octane rating of a gasoline fuel is to operate a standardized Cooperative Fuels Research (CFR) engine under conditions specified by industry standards (e.g., ASTM standards D2699-12 and D2700-12, incorporated herein by reference). An example of a modern CFR engine is the Waukesha CFR Combination Research and Motor Method Octane Rating Unit available from General Electric. CFR engines conventionally include a detonation pickup device, such as a magnetostrictive sensor, that generates an electrical signal that is proportional to the time rate-of-change of combustion chamber pressure in the engine while being run on a sample of the fuel under evaluation.

FIG. 1 illustrates a conventional CFR engine with the sensors involved in the conventional determination of KI for a fuel under evaluation. CFR engine 2 includes cylinder 4 within which piston 5 is disposed; piston 5 is mechanically coupled to crank 7 in the conventional manner. Fuel and air are mixed at carburetor 6 in the conventional manner, with the fuel received via an adjustable fuel supply 8, and intake air conditioned by intake air dehumidifier 9 and intake air heater 11. The fuel-air mixture is further heated by intake mixture air heater 13 and introduced into cylinder 4 at cylinder head 10 via the appropriate valve, near spark plug 14 that is also disposed at cylinder head 10. Exhaust gases from combustion are expelled from cylinder 4 via exhaust system 15. Starter motor 16 is provided to maintain a constant rotational speed of the engine system at the standard speed of 600 RPM (for the Research Octane Number, or RON, method) or 900 RPM (for the Motor Octane Number, or MON, method).

For purposes of evaluating the octane rating of fuels, detonation pickup 17 is mounted to the wall or head chamber of cylinder 4 of CFR engine 2, as shown in FIG. 1. Detonation pickup 17 is conventionally implemented as a magnetostrictive pressure rate-of-change transducer, which generates an electrical signal that is proportional to the time rate-of-change of combustion chamber pressure in cylinder 4. The height of cylinder head 10 of CFR engine 2 in this example is adjustable, which allows adjustment of the compression ratio of engine 2 and, indirectly, the nominal pressure inside cylinder 4. In addition, adjustable fuel supply 8 allows control of the air-fuel ratio supplied to engine 2. To evaluate a fuel sample, a control variable (typically the air-fuel ratio, or AFR) is varied while engine 2 is running, with detonation pickup 17 sensing knock events over that time interval. The industry standard test methods identify the peak time-rate-of-change of pressure as sensed by detonation pickup 17 as the peak knock intensity (KI), from which the octane rating of the fuel is determined. Typically, the KI of the fuel under evaluation is compared against the KIs of two primary reference fuels (PRFs), one PRF having a known high octane and the other PRF having a known low octane. The octane rating of the fuel under evaluation is typically calculated by linear interpolation between the octane ratings of the two PRFs, according to the relative KI of the fuel under evaluation relative to the KI values of the two PRFs.

Conventionally, other measurements besides the AFR, the height of cylinder head 10, and the output of detonation pickup 17 are also acquired at the standardized engine. As shown in FIG. 1 in connection with CFR engine 2, temperature sensor 18a senses the temperature of the heated intake air entering carburetor 6, temperature sensor 18m senses the temperature of the heated fuel-air mixture entering cylinder head 10, and barometer 19 measures the barometric pressure at CFR engine 2. As described by way of example in the ASTM MON Standard (D2700-12), these temperature measurements are conventionally used as feedback in the temperature control loop to maintain a constant temperature, and the barometric pressure measurement is used so as to adjust the cylinder head height to a normalized compression ratio (i.e., normalized to sea level).

As known in the industry, the price of gasoline varies with its octane rating, with higher octane rated-fuel commanding a higher price at the pump. Gasoline product as sold at a particular octane rating is typically blended to exhibit at least that octane rating when evaluated by a CFR engine such as that of FIG. 1. To the extent that error is present in the CRF test process, sufficient margin in the octane rating of the blended gasoline must be provided to ensure that all of the output meets the rated octane level. However, overblending (i.e., including more higher octane fuel in the blend than necessary for the octane rating at which it is sold) to provide this margin adds significant cost that will not be recovered in the price paid to the refiner, and is therefore not economically optimal.

BRIEF SUMMARY OF THE INVENTION

One or more embodiments of the invention provide a system and method of testing octane rating of a fuel in a test engine based on a multi-variable description of knock events, to more precisely estimate the octane rating value.

One or more embodiments of the invention provide such a system and method that incorporates environmental conditions into the determination of an octane rating of a test fuel, to improve the accuracy of the octane rating evaluation.

One or more embodiments of the invention provide such a system and method that incorporates measurements of engine and associated system conditions into the determination of an octane rating of a test fuel, to improve the accuracy of the octane rating evaluation.

One or more embodiments of the invention provide such a system and method that also predicts and issues notifications of maintenance issues.

Other objects and advantages of the various embodiments of the invention will be apparent to those of ordinary skill in the art having reference to the following specification together with its drawings.

According to certain embodiments, a test engine is operated to run on a plurality of fuels of known octane ratings (primary reference fuels, or PRFs), under conditions causing knocking. One or more sensors are deployed at the engine provide measurements related to the knock events, from which multiple measurement parameters regarding one or more knock events are obtained. Similar measurements at knock events are obtained from the engine running on a test fuel of unknown octane rating. Numerical processing is applied to these measurement parameters obtained from the running of the engine on the test fuel to determine the octane rating of that test fuel, according to relationships of values of those measurement parameters to octane ratings of the primary reference fuels.

According to certain embodiments, a test engine, such as a Cooperative Fuels Research (CFR) engine, is operated to run on a plurality of fuels of known octane ratings (primary reference fuels, or PRFs), over an interval in which an operational control variable (e.g., air-fuel ratio, or AFR) is varied to cause knock events. One or more sensors deployed at the engine provide measurements related to the knock events, from which multiple attributes, in addition to the peak knock intensity (KI), of each of a plurality of knock events are obtained. Similar measurements at knock events are obtained from the engine running on a test fuel of unknown octane rating. Statistical processing, such as a weighted averaging and interpolation, is applied to these multiple attributes, obtained during the tests of the PRFs and the test fuel, to obtain an octane rating for the test fuel.

According to certain embodiments, measurements are obtained during the operation of a test engine from a plurality of sensors including one or more sensors that provide measurements related to knock events, and one or more sensors for detecting environmental parameters at the engine, such as humidity, temperatures (e.g., one or more of intake gas, intake mixture, exhaust, combustion chamber), cylinder pressure, crank velocity or position, both types of sensors providing measurements while the engine is running on samples from a plurality of fuels of known octane ratings (primary reference fuels, or PRFs) under conditions at which knocking occurs. The measurements are stored in a database. The test engine is then operated on a sample of a fuel blend of unknown octane rating, over a range of the control variable, and the same measurements obtained. Statistical processing, such as a weighted averaging and interpolation, is applied to the measurements of the knock events and of the environmental parameters, obtained during the tests of the PRFs and the test fuel, to obtain an octane rating for the test fuel.

According to certain embodiments, measurements are obtained during the operation of a test engine from a plurality of sensors including one or more sensors that provide measurements related to knock events, and sensors that obtain measurements of the long-running properties of the test engine, while the engine is running on samples from a plurality of fuels of known octane ratings (primary reference fuels, or PRFs), over a range of a control variable (e.g., AFR). These other measurements include, for example, crank bearing vibration, cam bearing vibration, piston ring to cylinder wall vibration, valve travel, crankcase pressure, and the like. The measurements are stored in a database. The test engine is then operated on a sample of a fuel blend of unknown octane rating, over a range of the control variable, and the same measurements obtained. Statistical processing, such as a weighted averaging and interpolation, is applied to the measurements of the knock events and to the engine property measurements obtained during the tests of the PRFs and the test fuel, to obtain an octane rating for the test fuel. In addition, the engine property measurements are statistically analyzed to indicate the maintenance status of the CFR engine.

DETAILED DESCRIPTION OF THE INVENTION

The embodiments of the invention described in this specification are implemented into a system and method for evaluating the octane rating or octane number of a fuel, using a test engine such as the Cooperative Fuels Research (CFR) engine type, as it is contemplated that such implementation is particularly advantageous in that context. However, it is also contemplated that concepts of this invention may be beneficially applied to in other applications, including other techniques for evaluating the combustibility of fuels and other substances, and including the use of other engines and engine types that may or may not comply with a test standard or, indeed, may not even be considered as a "test" engine for the determination of octane rating. Examples of such alternative engines include fixed compression ratio engines with varying air-fuel ratio, ordinary high-compression motors, fuel-injected engines of various types, and the like. Accordingly, it is to be understood that the following description is provided by way of example only, and is not intended to limit the true scope of this invention as claimed.

Figure 2A:
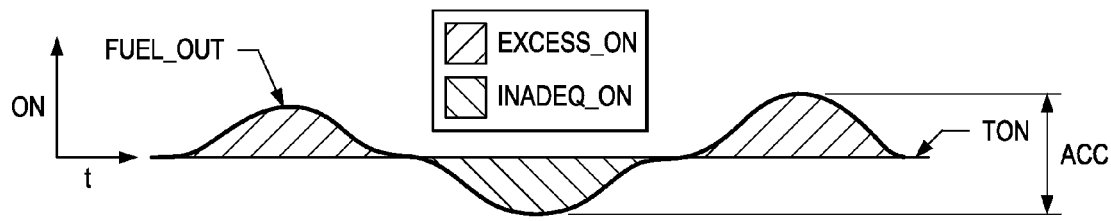
FIGS. 2a through 2d are plots of octane rating with fuel output over time illustrating the effect of conventional blending to attain a target octane rating.
Figure 2B:
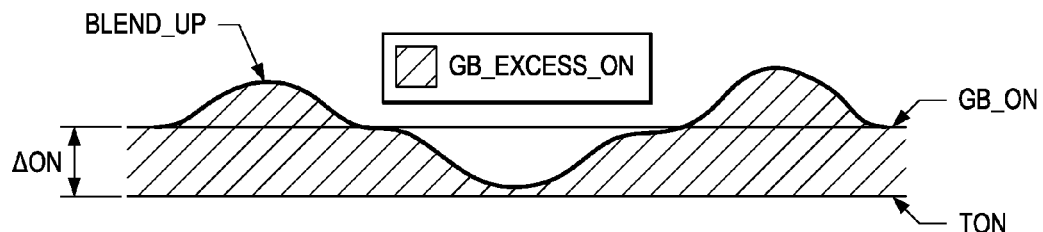

As mentioned above, imprecision in the measurement of the octane rating of fuels can lead to over-blending by the refiner to ensure that the fuel sold meets the specified octane rating. FIGS. 2a and 2d illustrate an example of the economic cost of this over-blending of refined fuel resulting from measurement of the octane rating (or octane number) by way of a standardized test engine according to conventional test standards. The plots of FIGS. 2a through 2b are qualitative plots of the octane number (ON) of each quantum of fuel output over time, relative to a target octane number (TON) specifying the octane rating at which the fuel is to be sold. As shown by plot FUEL_OUT of FIG. 2a, the actual octane number (ON) of the fuel varies, over time, above and below the target octane number TON, for example due to variations of the operating conditions at and of the standardized test engine over time, but within the accuracy ACC of the conventional octane rating test methods using a standardized test engine such as CFR engine 2.

While the refined fuel having an actual octane number ON above the target octane number TON (e.g., region EXCESS_ON in FIG. 2a) may be sold at the TON, the refined fuel having an actual octane number ON below the target octane number TON (region INADEQ_ON in FIG. 2a) cannot. To account for the inaccuracy of the measurements, the refiner will conventionally blend higher octane fuel with that output to ensure that all of the output will be saleable, as shown by plot BLEND_UP in FIG. 2b. Essentially, the octane number is raised by an amount $\Delta ON$ that is at least the difference between the target octane number TON and the lowest measured octane number of plot FUEL_OUT of FIG. 2a. This difference $\Delta ON$ is essentially a "guard band" of higher octane fuel to account for imprecision (i.e., accuracy ACC) in the conventional octane rating measurement process. As shown in FIG. 2b, much of the fuel (shown by regions GB_EXCESS_ON) will be sold at a lower octane rating, namely that of target octane number TON, than its actual measured octane number ON.

Figure 2C:
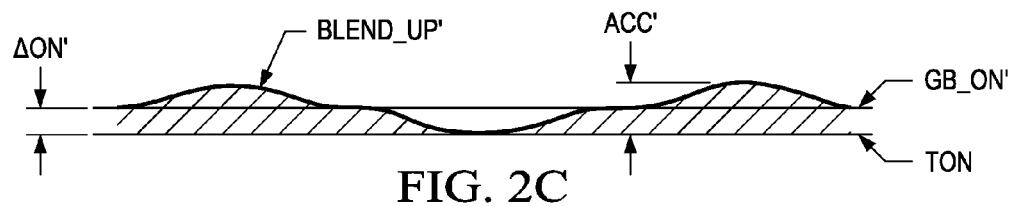
Figure 2D:
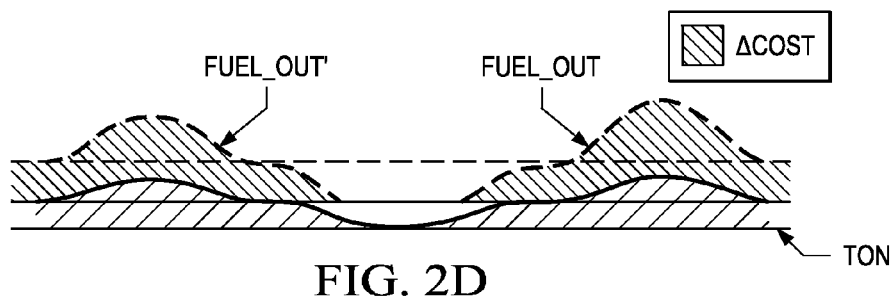

FIGS. 2c and 2d illustrate the potential economic benefit of improving the accuracy of the octane rating measurement from that shown in FIGS. 2a and 2b. In FIG. 2c, plot BLEND_UP' illustrates the measured octane number ON of fuel after the blending of higher octane fuel to raise all of the output above the target octane number TON, for a theoretical case in which the accuracy ACC' of the octane rating measurement process is improved from the accuracy ACC for the case illustrated in FIGS. 2a and 2b. As shown in FIG. 2c, the guard band $\Delta ON'$ by which the blending up of higher octane fuel raises the octane number of the output is much smaller than that of $\Delta ON$ of FIG. 2b, because of this improved accuracy. As a result, as shown in FIG. 2d, improved precision in the octane rating measurement can provide significant cost savings, as shown by region $\Delta COST$ corresponding to the area between plot FUEL_OUT of FIG. 2a and plot FUEL_OUT' of FIG. 2c, which are overlaid in FIG. 2d. Specifically, this improvement in measurement accuracy allows the refiner to optimize revenue by reducing the amount of higher octane fuel to be blended, while still ensuring that the octane rating of the fuel sold meets the desired requirements.

It has been discovered, in connection with this invention, that variables other than the control variables of air-fuel ratio (AFR) and cylinder head height can affect the combustibility of fuel in standardized engines to an extent that variation among these other variables can be a significant cause of imprecision in the octane rating determination. Embodiments of the invention as disclosed in this specification are directed to providing such an improvement in the accuracy of the measurement of octane rating in fuels for internal combustion engines by incorporating one or more of those other variables into the octane rating determination, as will now be described beginning with the system diagrams of FIGS. 3a and 3b.

Figure 1:
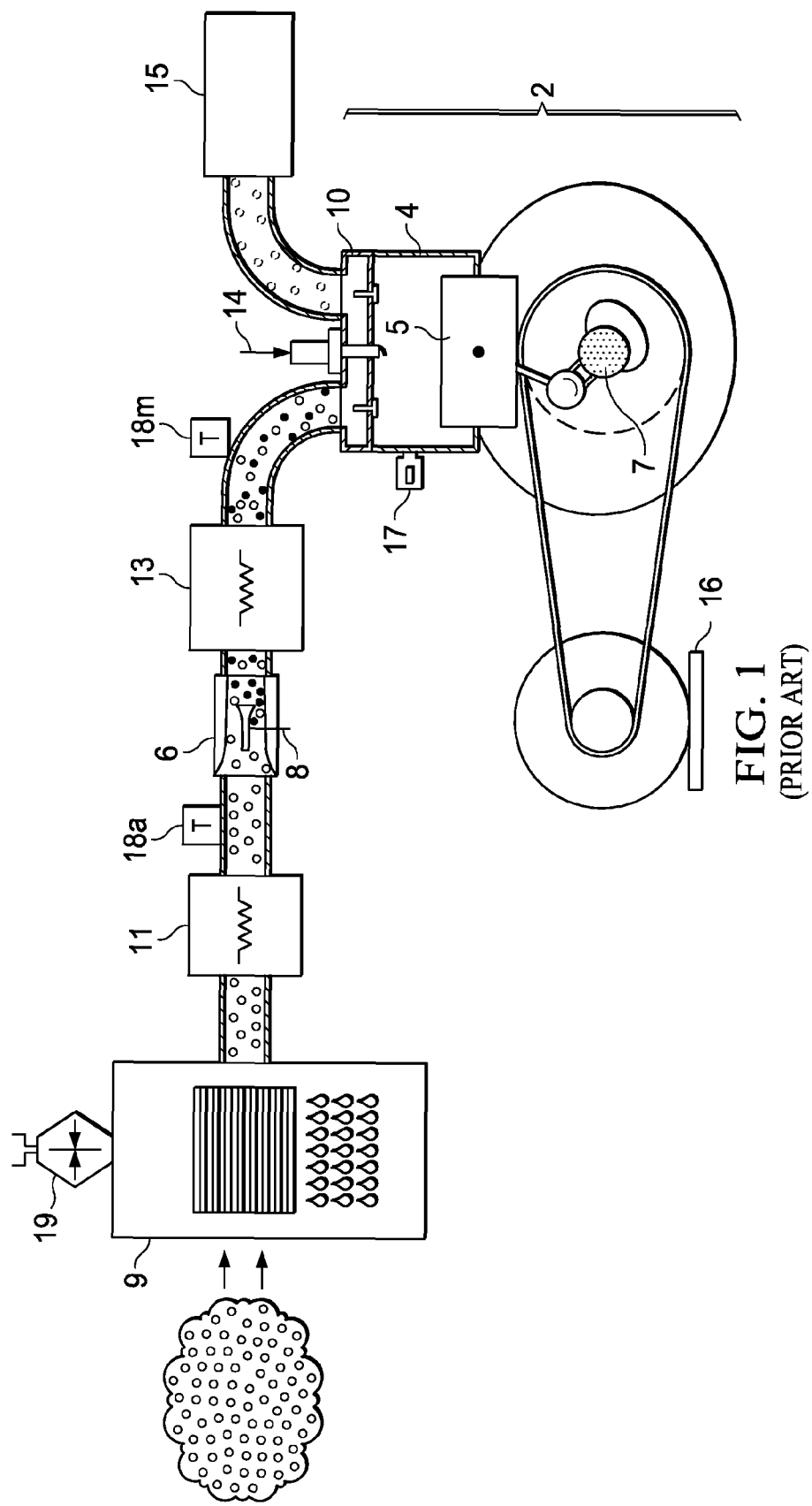
FIG. 1 is a mechanical diagram, in block form, illustrating the construction of a conventional test engine and corresponding sensors for determining the octane rating of a fuel.
Figure 3A:
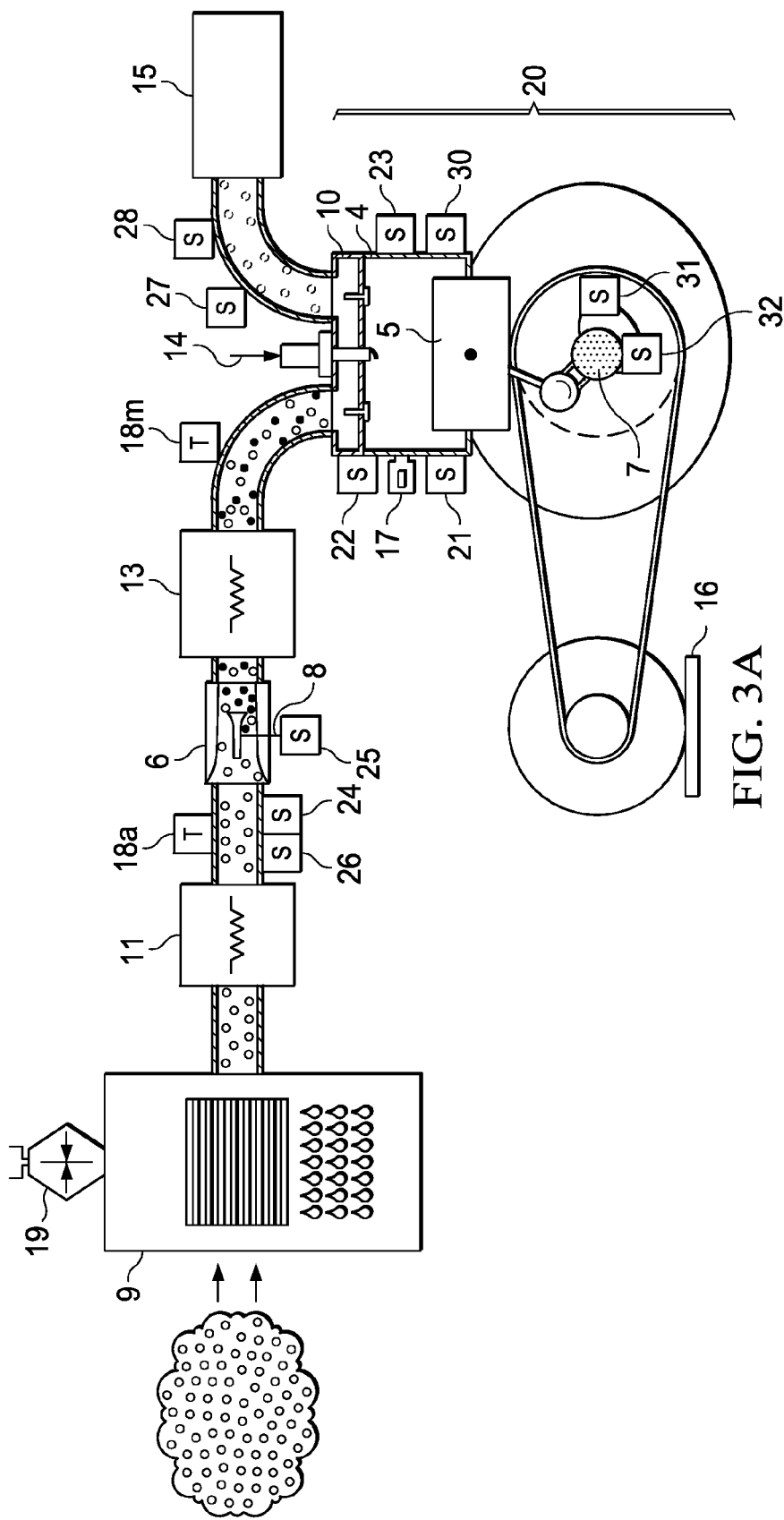
FIG. 3a is a mechanical diagram, in block form, illustrating the arrangement of sensors at a test engine, for determining the octane rating of a fuel according to embodiments of the invention.

FIG. 3a is a schematic diagram, in block form, of the implementation of additional sensors at a test engine 20, such as CFR engine 2 described above relative to FIG. 1, by way of an example of an embodiment of the invention. The construction and operation of CFR engine 20 as described herein will correspond largely to a conventional CFR engine as used to determine the "Motor Octane Number", or "MON", according to ASTM standard 2700-12, incorporated herein by reference; alternatively, CFR engine 20 may be constructed and operated so as to determine the "Research Octane Number", or "RON", according to ASTM standard 2699-12, also incorporated herein by reference, or as mentioned above may be a conventional high-compression motor, for example an engine with a fixed compression ratio and variable air-fuel ratio (AFR). Each of the elements and components shown in FIG. 1 in connection with CFR engine 2 that are included in CFR engine 20 of FIG. 3a are referred to by the same reference numeral. In that regard, magnetostrictive detonation sensor 17, intake air temperature sensor 18a, fuel-air mixture temperature sensor 18m, and barometer 19 are provided in this embodiment, as are sensors (not shown) indicating the control variables of cylinder head height and AFR. As will be described below, however, according to some embodiments of the invention, the signals from intake air temperature sensor 18a, fuel-air mixture temperature sensor 18m, and barometer 19 may be used in the calculation of the octane rating of the fuel under measurement, rather than merely as feedback in the temperature control loop or normalization of the cylinder head height to sea level. In addition, as will also be described below for some embodiments, attributes of the signals from magnetostrictive detonation sensor 17 indicative of the pressure-vs-time waveform other than the peak knock intensity will be analyzed and used in the calculation of the octane rating of the fuel under measurement.

It is contemplated that the engine with which embodiments of the invention may be used need not be a standardized test engine, such as CFR engine 20 shown in FIG. 3a and described above relative to FIG. 1, but may be any type of internal combustion engine. For example, while CFR engine 20 as shown in FIG. 3*a* is a carbureted engine, it is contemplated that embodiments of this invention may be used in connection with a fuel-injected engine. Such fuel-injected engines may utilize either mechanical or electronic control of the fuel injection system, and may inject fuel into an intake system or directly into the combustion chamber. As such, it is contemplated that this invention is not restricted to any particular type of engine, or to test or other standardized engines.

Various embodiments of the invention disclosed in this specification additionally may use measurements from other sensors that, according to those embodiments, are also deployed at or near CFR engine 20. According to some embodiments, additional sensors directed to the sensing of the knock event are deployed at CFR engine 20, such sensors including piezoelectric knock sensor 21 and cylinder pressure sensor 22. These additional sensors 21, 22 may be used, in these embodiments, in place of or in combination with magnetostrictive detection pickup 17 described above. However, as mentioned above and as will be described in further detail below, attributes of the signals from these sensors 17, 21, 22 beyond the peak KI will be incorporated into the octane number determination.

According to some embodiments of the invention, environmental conditions at or near CFR engine 20 are sensed and used in the determination of the octane rating of the fuel under measurement. These environmental condition sensors include intake air temperature sensor 18*a*, fuel-air mixture temperature sensor 18*m*, and barometer 19, as mentioned above. Examples of other sensors that may be deployed at CFR engine 20 for sensing of environmental conditions include cylinder wall temperature sensor 23, intake air flow (or air mass) sensor 24, fuel flow (or fuel mass) sensor 25, intake air humidity sensor 26, exhaust gas temperature sensor 27, exhaust oxygen sensor 28, and the like.

According to some embodiments of the invention, measurements of engine properties, such properties related to those conditions of CFR engine 20 itself that may affect the ignition of gasoline fuels, are obtained from additional sensors at CFR engine 20. Examples of these engine property sensors include cylinder wall vibration sensor 30, bearing vibration sensor 31, crank encoder 32 (i.e., indicating the position and velocity of crank 7 as it rotates), and the like. Cylinder pressure sensor 22, which is described above as one of the knock event sensors, can also serve as one of these engine property sensors, in that it can provide measurements of cylinder pressure at the bottom of the stroke and at top dead center, from which the compression ratio can be directly calculated. These engine properties as measured can be used in the determination of the octane rating of the fuel under measurement, according to these embodiments, and may also be monitored and analyzed to provide indications of the operating condition of CFR engine 20, including whether maintenance actions ought to be performed.

According to some embodiments of the invention, these and other similar or alternative measurements acquired from sensors at or near CFR engine 20, as may be implemented in a particular embodiment, are communicated to a computer system. An example of a system architecture suitable for processing these measurements for determination of the octane rating of a fuel under measurement according to embodiments of the invention is illustrated by computer system 40 of FIG. 3*b*.

Figure 3B:
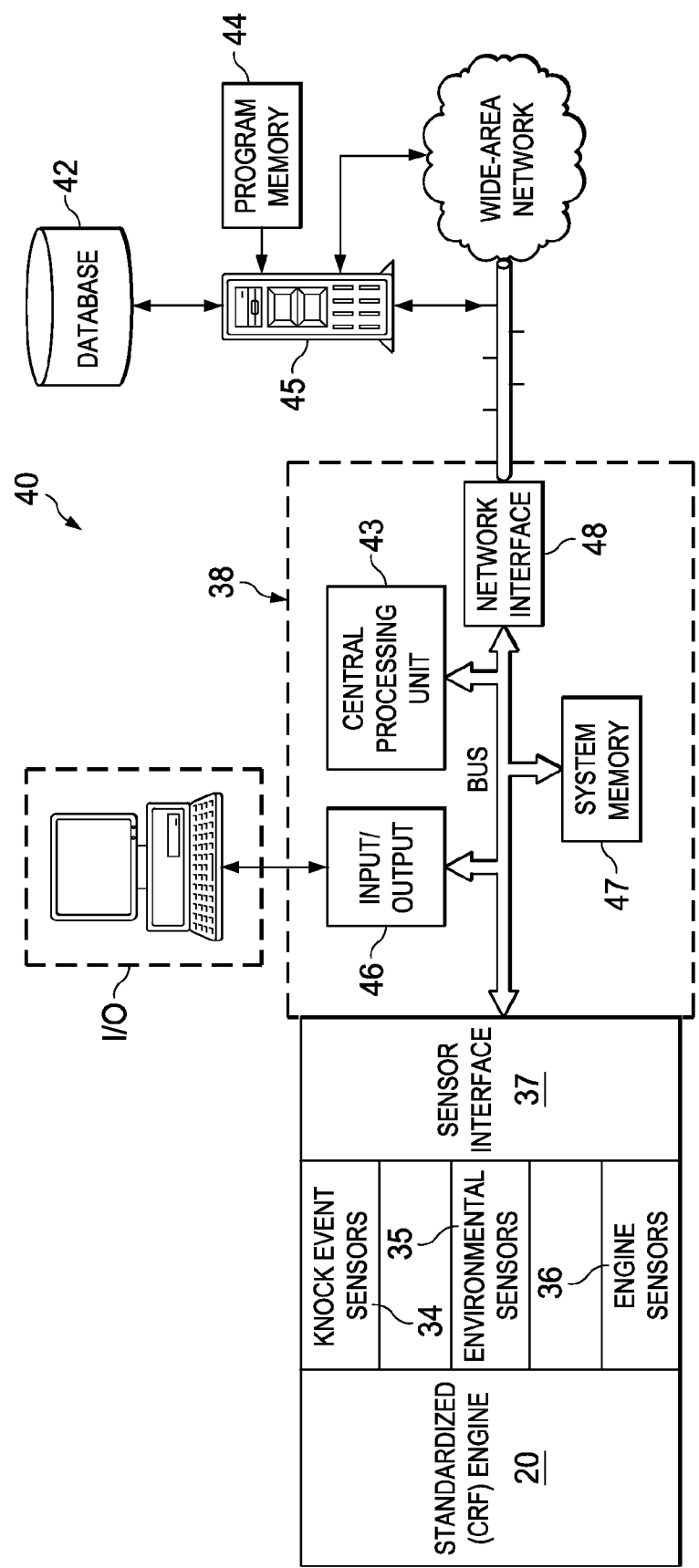
FIG. 3b is an electrical diagram, in block form, of a networked computer system programmed to execute various processes in the determination of octane ratings for fuels under measurement, according to one or more embodiments of the invention.

As shown in FIG. 3*b*, system 40 is realized in the form of a networked computer system including workstation 38 connected to server 45 by way of a network. Of course, the particular architecture and construction of system 40 useful in connection with these embodiments can vary widely. For example, system 40 may be realized by a single physical computer, such as a conventional workstation or personal computer, or alternatively by a computer system implemented in a distributed manner over multiple physical computers. Accordingly, the generalized architecture illustrated in FIG. 3*b* is provided merely by way of example.

As shown in FIG. 3*b* and as mentioned above, system 40 includes workstation 38 and server 45. Workstation 38 includes central processing unit 43, coupled to system bus BUS. Also coupled to system bus BUS is input/output interface 46, which refers to those interface resources by way of which peripheral functions I/O (e.g., keyboard, mouse, display, etc.) interface with the other constituents of workstation 38. Central processing unit 43 refers to the data processing capability of workstation 38, and as such may be implemented by one or more CPU cores, co-processing circuitry, and the like. The particular construction and capability of central processing unit 43 is selected according to the application needs of workstation 38, such needs including, at a minimum, the carrying out of the functions described in this specification, and also including such other functions as may be executed by system 40. In the architecture of system 40 according to this example, system memory 47 is coupled to system bus BUS, and provides memory resources of the desired type useful as data memory for storing input data and the results of processing executed by central processing unit 43, as well as program memory for storing the computer instructions to be executed by central processing unit 43 in carrying out those functions. Of course, this memory arrangement is only an example, it being understood that system memory 43 can implement such data memory and program memory in separate physical memory resources, or distributed in whole or in part outside of workstation 38.

Network interface 48 of workstation 38 is a conventional interface or adapter by way of which workstation 38 accesses network resources on a network. As shown in FIG. 3*b*, the network resources to which workstation 38 has access via network interface 48 includes server 45, which resides on a local area network, or a wide-area network such as an intranet, a virtual private network, or over the Internet, and which is accessible to workstation 38 by way of one of those network arrangements and by corresponding wired or wireless (or both) communication facilities. In this embodiment, server 45 is a computer system, of a conventional architecture similar, in a general sense, to that of workstation 38, and as such includes one or more central processing units, system buses, and memory resources, network interface functions, and the like. According to this embodiment of the invention, server 45 is coupled to program memory 44, which is a computer-readable medium that stores executable computer program instructions, according to which the operations described in this specification are carried out by system 40. In this embodiment of the invention, these computer program instructions are executed by server 45, for example in the form of an interactive application, upon data communicated from workstation 38, to create output data and results that are communicated to workstation 38 for display or output by peripherals I/O in a form useful to the human user of workstation 38. In addition, database 42 is also available to server 45 (and perhaps workstation 38 over the local area or wide area network), and stores such archival or reference information as may be useful in the operation of system 40 according to embodiments of the invention. This database 42 may reside on another local area network, or alternatively be accessible via the Internet or some other wide area network. It is contemplated that database 42 may also be accessible to other associated computers in the overall network.

Of course, the particular memory resource or location at which the measurements, database 42, and program memory 44 physically reside can be implemented in various locations accessible to system 40. For example, these data and program instructions may be stored in local memory resources within workstation 38, within server 45, or in network-accessible memory resources to these functions. In addition, each of these data and program memory resources can itself be distributed among multiple locations, as known in the art. It is contemplated that those skilled in the art will be readily able to implement the storage and retrieval of the applicable measurements, models, and other information useful in connection with this embodiment of the invention, in a suitable manner for each particular application.

As shown in FIG. 3b and as described above, various sensors are deployed at CFR engine 20. For purposes of this description, these sensors are grouped by function, namely knock event sensors 34 (including, without limitation, one or more of detonation sensor 17, piezoelectric knock sensor 21, and cylinder pressure sensor 22), environmental sensors 35 (including, without limitation, one or more of intake air temperature sensor 18a, fuel-air mixture temperature sensor 18m, barometer 19, cylinder wall temperature sensor 23, intake air flow sensor 24, fuel flow sensor 25, intake air humidity sensor 26, exhaust gas temperature sensor 27, and exhaust oxygen sensor 28), and engine property sensors 36 (including, without limitation, one or more of cylinder wall vibration sensor 30, bearing vibration sensor 31, and crank encoder 32). Each of sensors 34, 35, 36 are coupled to sensor interface 37, which in turn is coupled to workstation 38. Workstation 38 receives measurement inputs from sensor interface 37, including data corresponding to the measurements acquired by knock event sensors 34, environmental sensors 35, and engine sensors 36, for storage in a memory resource accessible to workstation 38, either locally or via network interface 48, and for subsequent processing.

Sensor interface 37 may be implemented as a conventional data interface as known in the art, for example as a semi-remote (i.e., a few to several feet away from CFR engine 20) data acquisition subsystem having cable connectors coupled to each of the sensors at CFR engine 20 for receiving the analog measurement signals. In such an implementation, sensor interface 37 may include some level of functionality for performing data collection (i.e., polling of sensors, analog-to-digital conversion, etc.), data conditioning (i.e., filtering, exclusion of outliers, etc.), and data packaging so as to forward the measurement data in a form suitable for receipt by workstation 38 via a conventional communication facility (e.g., USB, Ethernet, etc.). In addition, it is contemplated that sensor interface 37, or alternatively certain functionality at the sensors themselves, may carry out some level of numerical analysis on the received measurement data, examples of which will be described below.

Figure 3C:
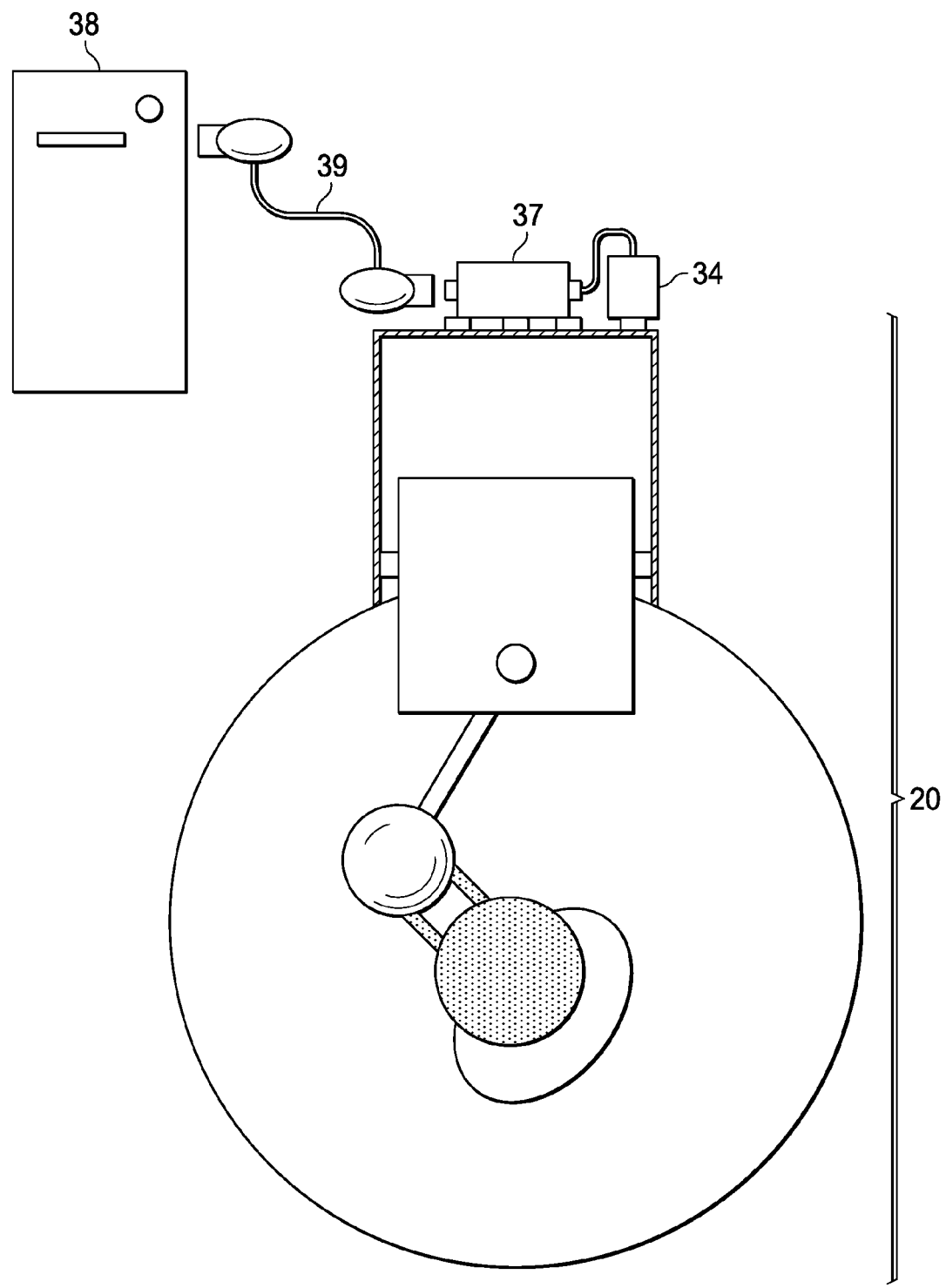
FIG. 3c is a mechanical diagram, in block form, illustrating the placement of a sensor interface module at a test engine, according to an embodiment.

FIG. 3c illustrates an implementation of sensor interface 37 according to an embodiment of the invention. In this implementation, sensor interface 37 is deployed as a module mounted directly to CFR engine 20 (e.g., to its framework), at a point near knock event sensors 34 and such other sensors, such as the environmental and engine property sensors noted above, from which it may gather measurements. This close proximity reduces attenuation and noise in the analog signals received from those sensors as compared with conventional data acquisition systems. In addition, according to this embodiment, sensor interface 37 is communications-powered from workstation 38, such as by way of powered USB or PoE (Power over Ethernet) facility 39 that couples sensor interface 37 to workstation 38. Sensor interface 37 in this embodiment includes the appropriate circuitry for acquiring and digitizing the immediate knock event signals from knock event sensors 34 (and such other sensors to which it is coupled), performs certain mathematical operations on those measurement data, for example as described below, and packages and transmits the measurement data to workstation 38, which will complete the octane rating determination. It is contemplated that the particular circuits implemented within sensor interface 37 will include the appropriate filter components, analog-to-digital conversion circuitry, communications transceiver circuitry, and programmable processing circuitry (with program and data memory) suitable for performing these functions; in that regard, it is contemplated that those skilled in the art having reference to this specification will be readily able to implement sensor interface 37 for performing these functions, without undue experimentation. The arrangement of sensor interface 37 of FIG. 3c according to this embodiment is believed to improve the accuracy of the octane rating determination by placing the digitizing electronics in the engine area, very close to the sensors from which it is receiving signals, so that noise from the environment and connections is greatly reduced. In addition, it is believed that this arrangement will also simplify the power and sensor connections, minimize footprint, and thus increase both the quantity of usable measurement data and its quality.

Referring back to FIG. 3b, and according to some embodiments of the invention, by way of example, system memory 47 and program memory 44 store computer instructions executable by central processing unit 43 and server 45, respectively, to carry out the functions described in this specification to determine the octane rating of a fuel under measurement at CFR engine 20. These computer instructions may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions may be written in a conventional high level language such as JAVA or C++, either as a conventional linear computer program or arranged for execution in an object-oriented manner. These instructions may also be embedded within a higher-level application. In any case, it is contemplated that those skilled in the art having reference to this description will be readily able to realize, without undue experimentation, this embodiment of the invention in a suitable manner for the desired installations. These executable computer programs for carrying out embodiments of this invention may be installed as resident within system 40 as described above, or alternatively may be in the form of an executable web-based application that is accessible to server 45 and client computer systems such as workstation 38 for receiving inputs from the client system, executing algorithms modules at a web server, and providing output to the client system in some convenient display or printed form. Alternatively, these computer-executable software instructions may be resident elsewhere on the local area network or wide area network, or downloadable from higher-level servers or locations, by way of encoded information on an electromagnetic carrier signal via some network interface or input/output device. The computer-executable software instructions may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by system 40 in the conventional manner for software installation.

Figure 4:
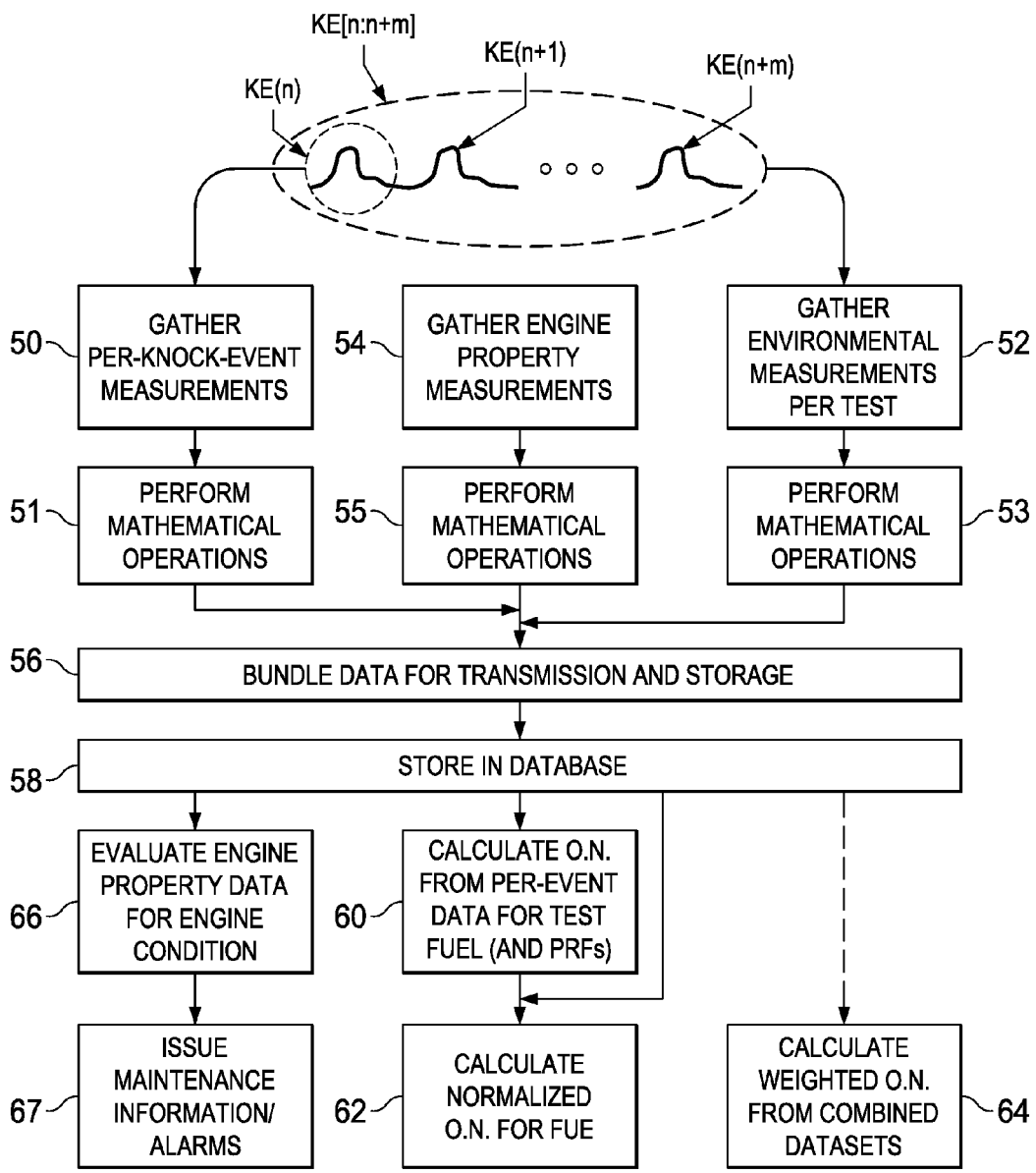
FIG. 4 is a flow diagram illustrating a method of determining the octane rating of fuels according to embodiments of the invention.

Referring now to FIG. 4, the data flow carried out by system 40 of FIG. 3b in determining octane rating for fuels via operation of a test engine such as CFR engine 20 described above, according to embodiments of the invention, will now be described. According to these embodiments, a wide range of measurements and observations can be incorporated into the determination of octane rating for a fuel under evaluation. These additional measurements and observations may correspond to additional observations regarding individual knock events beyond the peak knock intensity (KI) on which octane rating is determined, to measurements of environmental parameters at or near the test engine, or to properties and operational parameters regarding the test engine itself, or to a combination of those measurements and observations. The particular additional measurements and observations that are used may vary for different implementations of the various embodiments of the invention, depending on the nature and stability of the measurements gathered, the effects of particular measurements on the octane rating determination for a particular engine or implementation, the desired precision in the octane rating determination versus computational and measurement (i.e., sensor deployment) cost, and other factors that will be appreciated by those skilled in the art having reference to this specification.

In a general sense, the determination of the octane rating of a fuel according to embodiments of this invention is made from a set of measurements acquired from a test engine, such as a CFR engine, while running the fuel to be evaluated under such conditions that cause significant knocking (i.e., spontaneous ignition of the fuel-air mixture in latter portions of the combustion cycle). These measurements, for a given fuel, may be considered as a "fingerprint" of that fuel being evaluated, from which the octane rating of the fuel can be determined with a high degree of precision. In this regard, while the following description will specify a large number of particular measurements for accomplishing this function, it is contemplated that the particular measurements that are of significance in the octane rating determination may not necessarily be known a priori, but may only become apparent after obtaining a significant amount of data and results over a number of fuels, and under a number of environmental conditions for a particular engine. As will be discussed further below, it is contemplated that the precision of the octane rating determination can be attained by modification and adjustment of the particular calculations and results as the volume of measurement data and results increase with use. It is contemplated that those skilled in the art having reference to this specification will appreciate this nature of the embodiments of the invention.

For purposes of this specification, the particular processes carried out by system 40 to determine octane rating using these additional measurements and observations will be described with reference to the type of measurements involved. More specifically, this description will separately describe the processes of FIG. 4 as applied to measurements and observations pertaining to individual ("immediate") knock events; as applied to environmental measurements and observations; and as applied to engine property measurements and observations. As will then be further described in this specification, some embodiments may determine the octane rating of a fuel from a combination of measurements of different types, or from a combination of the octane rating results from measurements of those different types.

Immediate Knock Event Measurement Parameters

As known in the art, the octane rating determination process of embodiments of the invention is based on the operation of a test engine such as CFR engine 20 involves running the engine on a particular fuel to be evaluated while a control variable, typically AFR, is varied. As described above, conventional octane rating processes, such as described in the ASTM specifications noted above, use the peak knock intensity exhibited by those multiple knock events.

According to some embodiments, additional measurements and observations regarding individual knock events, beyond merely the peak knock intensity (KI) exhibited over the range that the AFR is varied, are used in the determination of octane rating. In the overall method shown in FIG. 4, this determination based on immediate knock event measurements begins with process 50, in which measurements are obtained from one or more of knock event sensors 34 deployed at CFR engine 20 of FIGS. 3a and 3b. As described above, knock event sensors 34 in this example include one or more of magnetostrictive detonation sensor 17, piezoelectric knock sensor 21, and cylinder pressure sensor 22. The measurements obtained in process 50 correspond to the time-varying signals output from the one or more of these knock event sensors 34 that are installed at CFR engine 20. For example, these measurements may be in the form of a sequence of sample values obtained from those sensors over a period of time including an individual knock event, at a sample rate sufficient to characterize the waveform of the sensed pressure or sound for a given knock event.

Figure 5A:
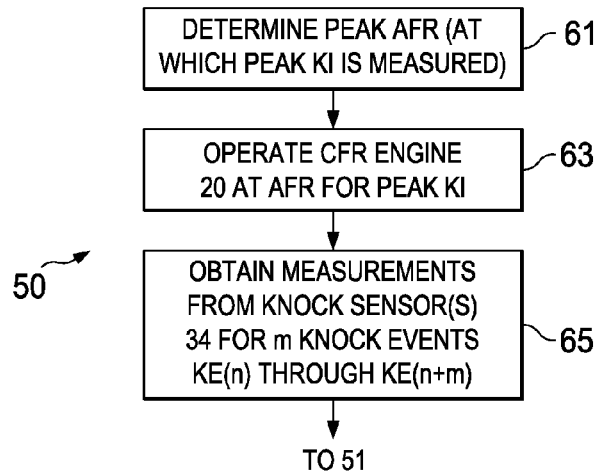
FIGS. 5a and 5b are flow diagrams illustrating the operation of the method of FIG. 4 in processing knock event measurement data, according to certain embodiments.

FIG. 5a illustrates, in further detail, an example of the manner in which measurement gathering process 50 is performed according to an embodiment of the invention. It is contemplated that process 50 will be performed using each of the fuels to be characterized, including both the high-octane and low-octane primary reference fuels (PRFs) and also the fuel under evaluation (FUE) for which the octane rating is to be determined. In this example, process 50 begins with process 61, in which CFR engine 20 is operated using a sample of one of the fuels with a control variable, typically AFR, modulated over a range that includes conditions at which knocking occurs. As known in the art, the conventional operation of a CFR engine to determine octane rating is performed by running the engine while modulating the AFR from a relatively lean condition to a relatively rich condition. Typically in conventional CFR engines, the AFR is indicated by a marked level in a sight glass or by an adjustment marking in a variable orifice, and as such a precise measurement of AFR is typically not known in conventional CFR engines. CFR engine 20 may be operated in a similar fashion, in process 50 according to some of the embodiments of the invention. In cases where the AFR will not be precisely known, CFR engine 20 may simply be operated under conditions (e.g., at an AFR and compression ratio or cylinder height) at which significant knocking occurs.

According to some embodiments, additional sensors such as intake air flow (air mass) sensor 24 and fuel flow (fuel mass) sensor 25 are deployed at CFR engine 20 as noted above. These sensors 24, 25 permit determination of a precise AFR value. According to these embodiments, including the embodiment of measurement gathering process 50 shown in FIG. 5*a*, the AFR at which the knock intensity (KI) is at its peak, i.e. the AFR at which CFR engine 20 has the worst knocking for that particular fuel, is determined in process 50. If multiple knock event sensors 34 are being used, the determination of this AFR at peak KI in process 61 may be made using one of those sensors (e.g., detonation pickup 17), or alternatively from some average or combination of the results from multiple such sensors 34, in combination with the sensors measuring AFR.

Alternatively, process 61 may be performed simply to identify an operating condition of CFR engine 20 at which significant knocking occurs (i.e., of sufficient intensity as to provide confidence in the knock event measurements), but without necessarily identifying the AFR at peak KI, as noted above.

In process 63, CFR engine 20 is operated at this AFR (i.e., at peak KI or such other AFR identified in process 61 as causing significant knocking) for some duration of time. During this operation of process 63, measurements are acquired from each of knock event sensors 34 for a series of knock events. For example, data collection from a given knock event sensor 34, for an individual knock event KE(n) may be triggered on the rising edge of the signal from the sensor for that event. FIG. 4 illustrates this series of m knock events KE(n) through KE(n+m) for which measurements are obtained from each of the one or more knock event sensors in process 65. As noted above, the measurements obtained in the process 65 are contemplated to be a series of sample values obtained from each knock event sensor 34 over a period of time including each of the m individual knock events at the appropriate sample rate. According to this implementation of measurement gathering process 50, the number of measurements of knock events is intended to provide statistical confidence in the determination of attributes of the knock event waveforms.

Alternatively, measurement gathering process 50 may be simply be based on a single knock event at a single AFR or on multiple knock events at different AFRs during the operation of CFR engine 20, depending on the fidelity of the knock event waveform shape and other implementation details.

Referring back to FIG. 4, following measurement gathering process 50, process 51 is then performed by system 40 to apply certain mathematical operations to analyze the knock event measurements acquired in process 50. As discussed above, it is contemplated that sensor interface 37 includes the appropriate processing capability for executing the operations of process 51 on the sample sequences from knock event sensors 34, prior to forwarding these measurement data to workstation 38. Alternative arrangements in which the sample sequences are forwarded to workstation 38, which carries out the operations of analysis process 51, and alternative arrangements in which the operations of analysis process 51 are performed by processing capability at knock event sensors 34 themselves, are also contemplated.

Figure 5B:
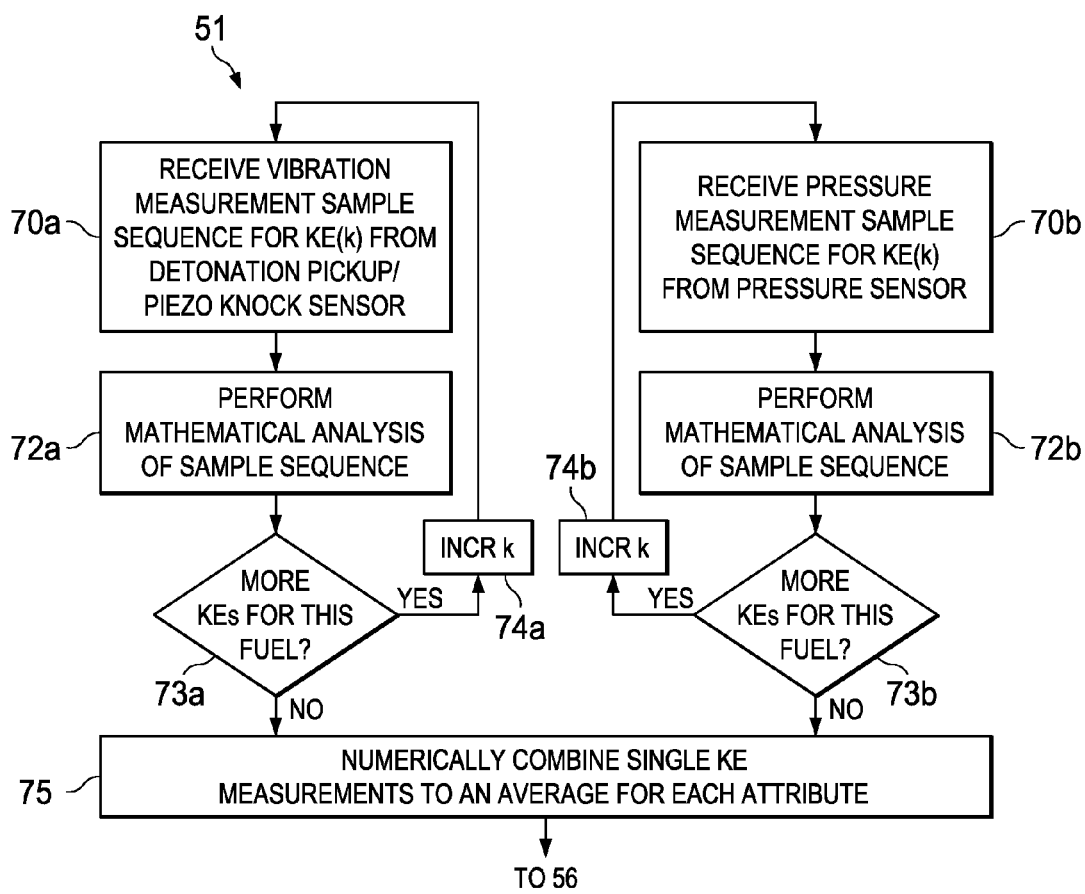
Figure 5C:
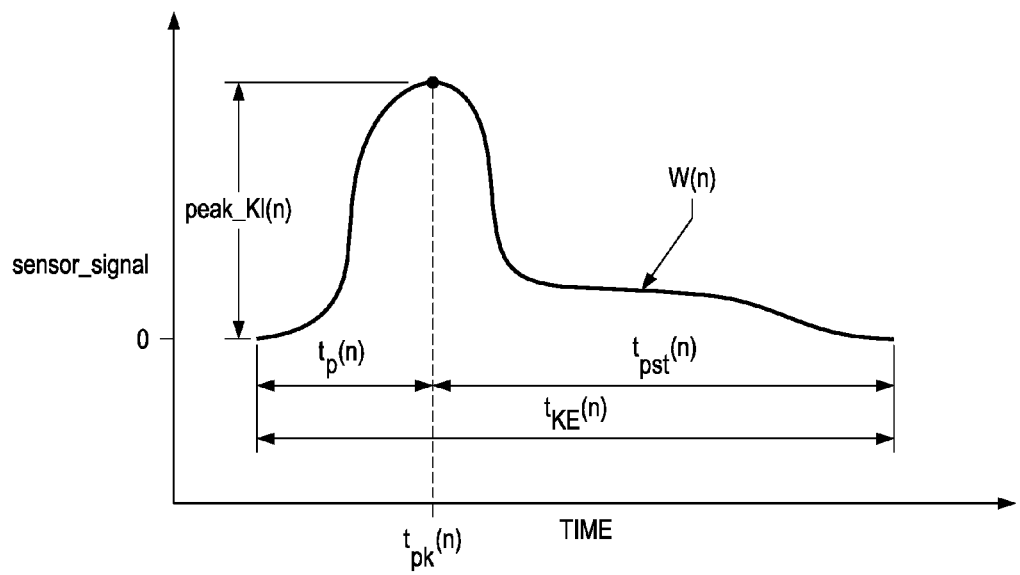
FIG. 5c is an illustration of a knock event waveform, showing various attributes of the waveform as used in the method of FIGS. 5a and 5b.

FIGS. 5*b* and 5*c* illustrate an example of the manner in which analysis process 51 is performed to apply certain mathematical operations to the received measurement sample sequences, according to an embodiment. In process 70*a* (FIG. 5*b*), the vibration measurement sample sequence for one knock event KE(k), from one of the knock event sensors 34 of the vibration type (i.e., detonation pickup 17 or piezoelectric knock event sensor 21) is received by sensor interface 37. In this embodiment, this knock event KE(k) corresponds to one of the knock events in the series of m knock events KE(n) through KE(n+m) at the AFR at peak KI identified in process 61, for one of the fuels. Process 70*a* may be performed by sensor interface 37 asynchronously receiving the samples as acquired, for example as triggered by a leading edge of a knock event as sensed by that knock event sensor 34, or by retrieving the sample sequence from memory.

In process 72*a*, sensor interface 37 analyzes the sample sequence received in process 70*a* to identify one or more attributes of the waveform represented by that sample sequence. FIG. 5*c* illustrates an example of waveform W(k) of sensor output signal sensor_output versus time, as represented by the sample sequence received in process 70*a* for knock event KE(k). In this illustration of FIG. 5*c*, waveform W(n) is shown in the form of an analog waveform, for clarity; as noted above, it is contemplated that the sample rate of knock event sensor 34 will be sufficient to capture the attributes of the waveform W(k) that are sought to be identified in this process 72*a*. Certain conventional filtering of the sensor output may also be performed as part of process 72*a*, prior to the particular mathematical operations for identifying attributes described below.

Certain attributes of waveform W(k) that may be determined from the analysis of process 72*a* are shown qualitatively in FIG. 5*c*, by way of example. As shown in FIG. 5*c*, the value peak_KI(k) represents the peak value of the sensor output sensor_signal (i.e., the peak knock intensity) for this knock event KE(k), and peak time $t_{pk}(k)$ is the time at which this peak_KI(k) was sensed. The time duration of the captured signal corresponding to knock event KE(k) is shown by the value $t_{KE}(k)$, with $t_p(k)$ representing the time duration of the captured signal from the beginning of knock event KE(k) to peak time $t_{pk}(k)$, and $t_{pst}(k)$ representing the time duration of the captured signal from peak time $t_{pk}(k)$ to the end of knock event KE(k). Other attributes of waveform W(k) that may be determined in process 72*a* may include:

Total captured signal calculated Discrete Fourier Transform (DFT)
  Integral value of total captured signal
  Integral of pre-peak signal
  Integral of post-peak signal
  $1^{st}$ derivative of captured signal—average acceleration of pressure (from detonation pickup 17 and piezoelectric knock sensor 21)
  $1^{st}$ derivative of captured signal—velocity (from cylinder pressure sensor 22)
  $2^{nd}$ derivative of captured signal—acceleration (from cylinder pressure sensor 22)
  Calculated average of captured signal data values
  Calculated Mean value of captured signal data values
  Calculated Median value of captured signal data values
  Calculated Standard Deviation of captured signal data values
  Signal width at ⅓ peak value, prior to peak value
  Signal width at ½ peak value, prior to peak value
  Signal width at ⅔ peak value, prior to peak value
  Signal width at ⅓ peak value, post peak value
  Signal width at ½ peak value, post peak value
  Signal width at ⅔ peak value, post peak value Process 72*a* determines one or more of these attributes for knock event KE(k) by way of conventional data processing operations, as will be familiar to those skilled in the art having reference to this specification.

Following process 72*a*, decision 73*a* is performed by sensor interface 37 to determine whether more knock events remain to be analyzed by process 51 in the series of m knock events KE(n) through KE(n+m) for this fuel; if so (decision 73a is "yes"), index k is incremented in process 74a, and processes 70a, 72a and decision 73a are repeated for that next knock event, until all knock events in the series of m knock events KE(n) through KE(n+m) for this fuel, as measured by this knock event sensor 34, have been analyzed (decision 73a returns a "no" result).

As discussed above, multiple knock event sensors 34 may be deployed at CFR engine 20 and used in the determination of octane rating according to this embodiment. If a second vibration-type knock event sensor 34 is so used (e.g., if both detonation pickup 17 and piezoelectric knock event sensor 21 are implemented), then the loop of processes 70a, 72a and decision 73a are also performed for the vibration measurement sample sequence for the same series of m knock events KE(n) through KE(n+m) for the same fuel type, as acquired by that other vibration-type knock event sensor 34. If cylinder pressure sensor 22 is implemented at CFR engine 20, a similar loop of processes 70b, 72b and decision 73b is performed by sensor interface 37 as part of analysis process 51. In that embodiment, these processes 70b, 72b and decision 73b are carried out in much the same manner as described above for the processes 70a, 72a and decision 73a, except that the sample sequences analyzed are pressure measurements rather than vibration measurements.

In any case, upon completion of processes 70a/b, 72a/b (decisions 73a/b return a "no" result) for measurements from all knock event sensors 34 for a series of m knock events KE(n) through KE(n+m) for a given fuel type, a dataset representative of those attributes of the waveforms for each of those knock events, from each sensor, has been obtained. If data were acquired from more than one knock event sensor 34, process 75 may then be performed to numerically combine, for each knock event, the same waveform attributes as measured by these multiple sensors 34 according to some type of average (perhaps in a weighted fashion to account for the relative accuracy of those sensors, etc.). Alternatively, process 75 may be omitted, in which case the attributes as measured by knock event sensors 34 will be maintained as separate from one another. The resulting set of waveform attributes are then forwarded to process 56 (FIG. 4), for the bundling of those data into a form suitable for transmission to and storage by workstation 38 or another memory resource in system 40.

Octane Rating Determination

As shown in FIG. 4 according to this embodiment, the bundled measurement data transmitted by sensor interface 37 in process 56 are stored by or via workstation 38 in one of the memory resources (e.g., system memory 47, network database 42) that is maintaining a database of these measurements, in process 58. Following this database storage of process 58, the measurement data are retained in that memory resource until such time as a user or automated process retrieves those data to determine an octane rating for a fuel under evaluation (FUE). Various embodiments of this invention perform that octane rating determination according to various approaches, examples of which will now be described with reference to FIGS. 6a through 6c.

For the determination of octane rating from measurement data produced from one or more knock event sensors 34, as described above relative to FIGS. 5a through 5c, process 60 is executed by programmable processing circuitry in system 40 (e.g., by central processing unit 43 of workstation 38, or by one or more CPUs in server 45), from program instructions stored in and retrieved from the appropriate program memory source. As will be apparent from this description, the particular manner in which process 60 is carried out on measurement data from knock event sensors 34 may also be applied to measurement data from other sensor types, including environment sensors 35 and engine property sensors 36. Accordingly, while the following description of these operations will be described in the context of process 60 as applied to knock event measurement data, it is to be understood that these same operations may also be applied, as appropriate, to measurement data from those other sensors at CFR engine 20.

The determination of octane rating for an FUE, according to embodiments of this invention, is performed by a comparison of the operation of CFR engine 20 while running the FUE, to the operation of CFR engine 20 while running certain primary reference fuels (PRFs), which are fuels of known octane rating. Typically, these PRFs will include at least a high octane PRF and a low octane PRF. As such, this determination requires gathering and processing of measurement parameters for which values were acquired during the operation of CFR engine 20 for each of those fuels. The following description, as applied to parameters measured by knock event sensors 34, thus assumes that processes 50, 51, 56, 58 have been performed on such measurement parameters from at least those three runs of fuel by CFR engine 20.

In summary, and as noted above, process 60 involves numerical operations executed by the appropriate processing unit to determine the octane rating of the FUE relative to that of the PRFs. In a general sense, this numerical processing is performed according to relationships of parameters as measured at CFR engine 20 while running the PRFs, to the octane ratings of those PRFs. These relationships are not necessarily explicit expressions, and in some cases may not even be expressible, but may instead be heuristics or statistically-based, according to the experiential data gathered over time and over a range of operating conditions. It is contemplated that a number of statistical and numerical approaches to performing this determination from the available measurement data may be used to carry out this process 60. Two such approaches to carrying out process 60 will be described below, it being understood that these approaches are presented by way of example only, and are not to be considered in a limiting sense.

Interpolation from Multiple Single-variable Estimates

Figure 6A:
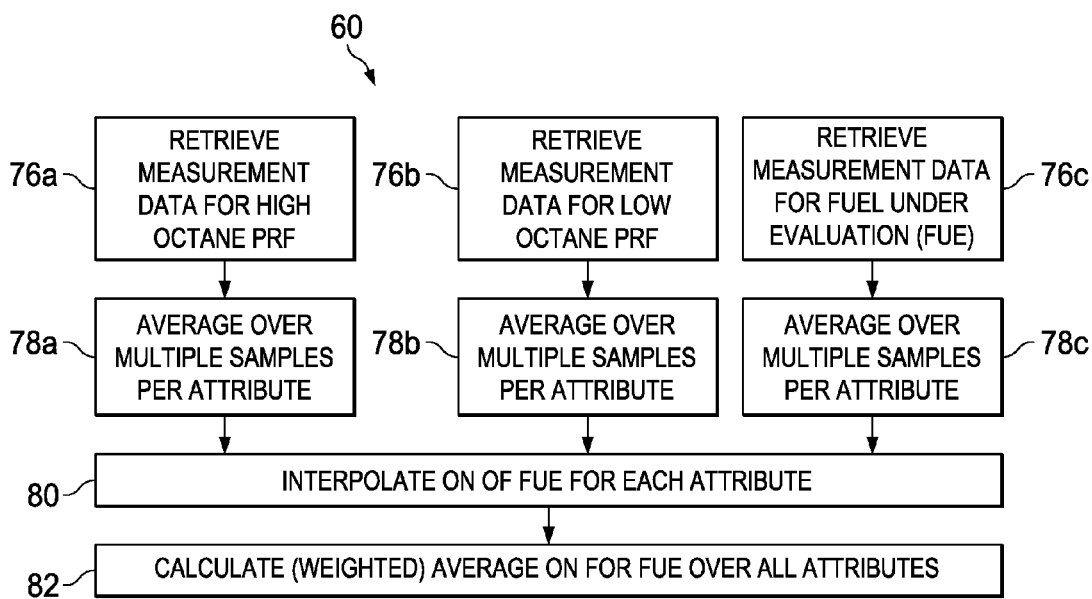
FIG. 6a is a flow diagram illustrating the operation of the method of FIG. 4 in determining the octane ratings of fuels from knock event measurement data, according to an embodiment.
Figure 6B:
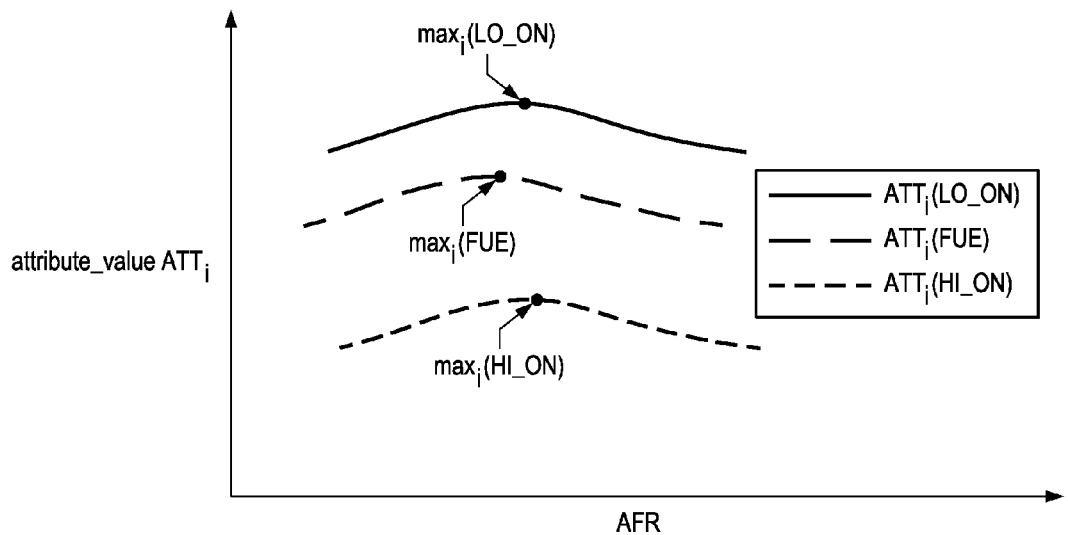
FIG. 6b is a plot illustrating an example of interpolation as applied in the method of FIG. 6a according to that embodiment.

According to one approach to the implementation of process 60, the measurement data from knock event sensors 34, including the waveform attributes generated in process 51, as stored in a database via process 58, are processed to derive an interpolation of the octane rating for the FUE, from the data for the high octane and low octane PRFs. FIGS. 6a and 6b illustrate an example of this approach.

In this embodiment, as shown in FIG. 6a, process 60 begins with the retrieval from memory of data corresponding to measurement parameters obtained in processes 50, 51. The data pertaining to one or more instances of CFR engine 20 running on the high octane PRF are retrieved in process 76a, data pertaining to one or more instances of CFR engine 20 running on the low octane PRF are retrieved in process 76b, and data pertaining to one or more instances of CFR engine 20 running on the FUE are retrieved in process 76c.

According to the embodiment described above in which waveform attributes are determined for each of a series of m knock events KE(n) through KE(n+m), processes 78a, 78b, 78c are then performed to combine those waveform attributes from the individual m knock events KE(n) through KE(n+m) for the high octane PRF, low octane PRF, and FUE into some sort of average or other statistical representation over that series for each of those fuels For example, processes 78a/b/c may simply calculate an unweighted average for each attribute over the series of waveforms W(n) through W(n+m); alternatively, processes 78a/b/c may perform some type of weighted average or other statistical calculation in order to derive an average value for each attribute. If multiple FUEs are being evaluated, processes 78a, 78b may be performed in advance.

Of course, if the waveform attributes retrieved in processes 76a/b/c pertain to only a single knock event for any of those fuels, corresponding processes 78a/b/c will be omitted.

In process 80, an octane number interpolation to determine an octane number (ON) for the FUE relative to the octane numbers for the low octane and high octane PRFs, based on each of the attributes retrieved in processes 76a/b/c. FIG. 6b qualitatively illustrates curves of an attribute value $ATT_i$ for a waveform attribute i (e.g., peak knock intensity) versus AFR for three fuels, namely curve $ATT_i$(LO_ON) for the low octane PRF, curve $ATT_i$(HI_ON) for the high octane PRF, and curve $ATT_i$(FUE) for the fuel under evaluation (FUE). While the AFR is not necessarily varied in the data retrieved in processes 76a/b/c, the curves of FIG. 6b serve to illustrate the relative behavior of this attribute value $ATT_i$. For purposes of interpolation process 80, one point may be selected for each of the three fuels, such as the maximum attribute values $max_i$(LO_ON), $max_i$(HI_ON), and $max_i$(FUE) for the three fuels as indicated in FIG. 6b. As evident from FIG. 6b, the AFR at which these maximum attribute values $max_i$(LO_ON), $max_i$(HI_ON), and $max_i$(FUE) are taken may not be the same among the three fuels. In this embodiment, interpolation process 80 linearly interpolates an octane number for the FUE relative to the known octane numbers for the low octane and high octane PRFs, according to the relationship of the maximum attribute value $max_i$(FUE) within the range between the attribute values $max_i$(LO_ON) and $max_i$(HI_ON). This interpolation process 80 is separately performed for each of the attributes to be considered in the octane rating determination.

Following interpolation process 80 for each of the relevant attributes, process 82 is then performed to calculate an octane rating for the FUE from the set of interpolated octane numbers from that process 80. According to this embodiment, process 82 may be performed by way of an averaging process. This averaging may be an unweighted arithmetic mean of the interpolated octane numbers from process 80, or may be a weighted averaging of those interpolated octane numbers, with the weights being derived according to previously determined measures of relevance, such as from an analysis of variance determination, relative accuracies of the attributes as determined, relative accuracies of or other weighting factors for the particular knock event sensors 34, and the like. Other statistical measurements may also go into the calculation of the octane rating in process 82. In any case, process 82 returns an octane rating for the FUE as based on multiple attributes from the measurement of immediate knock events, as sensed by one or more knock event sensors 34.

Applying a Multi-variable Expression for Octane Number

Figure 6C:
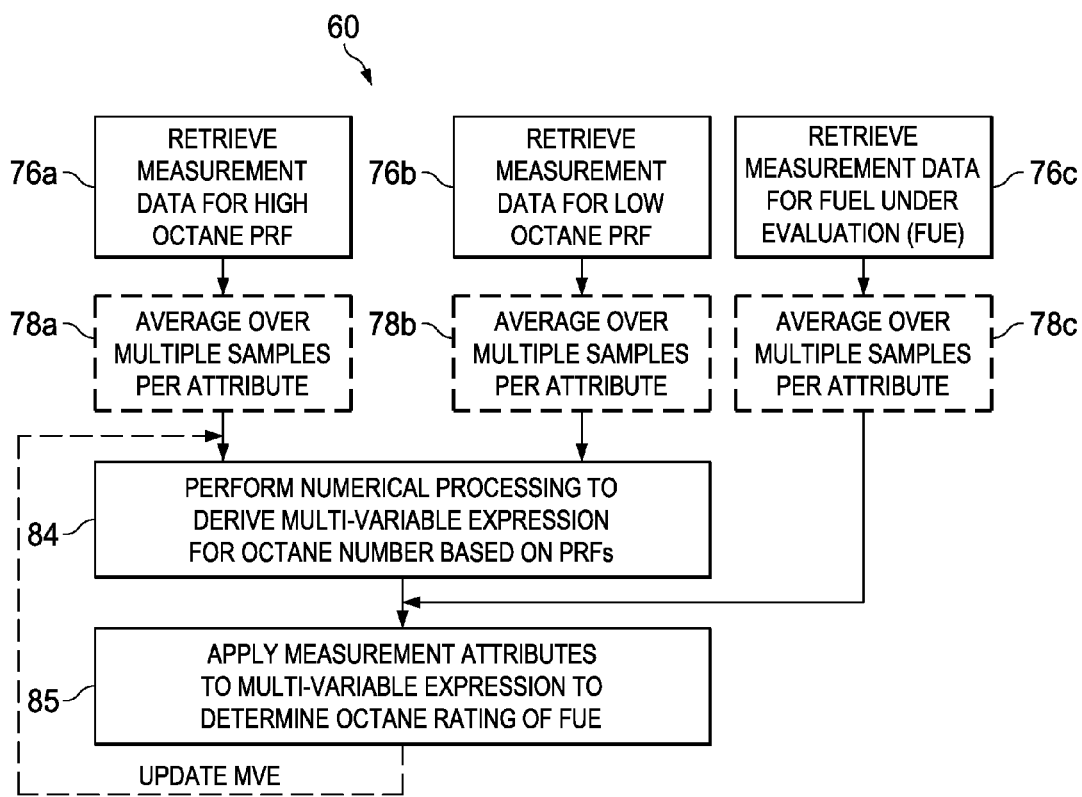
FIG. 6c is a flow diagram illustrating the operation of the method of FIG. 4 in determining the octane ratings of fuels from knock event measurement data, according to another embodiment.

FIG. 6c illustrates another approach to the octane rating determination process 60, according to another embodiment of the invention. As in the embodiment described above relative to FIG. 6a, data pertaining to one or more instances of CFR engine 20 running on the high octane PRF are retrieved in process 76a, data pertaining to one or more instances of CFR engine 20 running on the low octane PRF are retrieved in process 76b, and data pertaining to one or more instances of CFR engine 20 running on the FUE are retrieved in process 76c. If waveform attributes are determined for each of a series of m knock events KE(n) through KE(n+m), processes 78a, 78b, 78c are then performed to combine those waveform attributes from the individual m knock events KE(n) through KE(n+m) for the high octane PRF, low octane PRF, and FUE into some sort of average or other statistical representation over that series for each of those fuels.

In process 84, numerical processing is performed on the attributes for the low octane PRF and the high octane PRF, for which the octane numbers are known, to derive a multi-variable expression for octane number as a function of attribute data values. It is contemplated that any one of a number of conventional statistical and numerical techniques may be performed in this process 84 to derive such a multi-variable expression. Examples of such techniques include conventional analysis of variance (ANOVA) techniques by way of which the relative effects of variables (i.e., the waveform attributes) on an output value (i.e., octane number) are determined; other statistical approaches; so-called "fuzzy logic" algorithms; adaptive network algorithms, and other "artificial intelligence" techniques. In any case, the result of process 84 is an expression, whether in an explicit form or embedded in logic circuitry or other algorithms, relating the waveform attribute values for the PRFs to their known octane numbers.

In process 85, the attribute values for the FUE that were retrieved in process 76c and averaged in process 78c (if applicable) are applied to the multivariable expression derived in process 84, according to which an octane number for the FUE is calculated.

Optionally, the results of process 85 for the FUE are used to update the multi-variable expression of process 84, as suggested in FIG. 6c. By way of this updating with results as obtained through the use of this approach, a database of octane rating versus the various attributes of the knock events can be constructed over time, and the multi-variable expression or statistics improved as a result. It is contemplated that this construction of a database and the resulting statistical or numerical relationships can provide greatly improved accuracy in the octane rating determination, reducing the need to frequently run CFR engine 20 on PRFs as is required for conventional methods.

Similarly, referring to the interpolation approach of FIG. 6a described above, the database may be updated with the results of the interpolated octane rating, to provide additional interpolation points that can be applied to other fuels being evaluated and thus improve the accuracy and precision of the octane rating determination.

According to these and other approaches to performing numerical processing process 60 of FIG. 4 according to these embodiments, an octane rating (i.e., octane number) for the fuel under evaluation FUE is determined, based on the multiple attributes of the knock event waveforms as sensed by knock event sensors 34. It is contemplated that the use of attributes other than merely the peak knock intensity (KI), as conventionally used in connection with the ASTM standards referenced above, can provide additional precision and accuracy in the octane rating determination, and can result in a more efficient octane rating procedure.

Environmental Measurement Parameters

According to some embodiments, as described above relative to FIGS. 3a and 3b, environmental sensors 35 are provided at CFR engine 20 to measure various environmental parameters during its operation while running the various fuels. As described above, these environmental sensors 35 may include intake air temperature sensor 18a, fuel-air mixture temperature sensor 18m, and barometer 19, cylinder wall temperature sensor 23, intake air flow (or air mass) sensor 24, fuel flow (or fuel mass) sensor 25, intake air humidity sensor 26, exhaust gas temperature sensor 27, exhaust oxygen sensor 28, and the like. Other environmental measurement parameters that may be of interest in connection with this embodiment, and for which corresponding environmental sensors may be installed at CFR engine 20, include oil temperature, coolant temperature, fuel pressure, crankcase pressure, and the like. Indeed, some sensors 34, 35, 36 may be considered as providing readings for multiple functions; for example, crank encoder 32 may provide both an environmental measurement parameter and also an engine property measurement parameter (as will be described below). In operation, referring to FIG. 4, measurements of the parameters sensed by these environmental sensors 35 that are deployed at or near CFR engine 20 are obtained in process 52 over the duration of one or more knock events KE for each fuel (e.g., over the series of m knock events KE[n:n+m] as shown in FIG. 4).

In process 53 (FIG. 4), the appropriate circuitry in sensor interface 37 digitize the signals output by environmental sensors 35 and perform certain mathematical operations on those environmental measurement data. It is contemplated that these operations will typically include some type of time-averaging of the measurement parameter values from each sensor 35, at least over the relatively short time corresponding to the series of knock events of interest; this time-averaging and other processing of process 53 will be performed separately for each of the fuels (i.e., high octane PRF, low octane PRF, and fuel under evaluation FUE), to keep the environmental measurement parameters separated in that manner. In process 56, as described above, sensor interface 37 packages and transmits the environmental measurement parameter data to workstation 38, which in turn stores those data in memory in process 58.

Engine Property Measurement Parameters

According to some embodiments, as described above relative to FIGS. 3a and 3b, engine sensors 36 are provided at CFR engine 20 to measure various engine property parameters during its operation while running the various fuels. As described above, these engine property sensors 35 may include cylinder wall vibration sensor 30, bearing vibration sensor 31, crank encoder 32 (i.e., indicating the position and velocity of crank 7 as it rotates), cylinder pressure sensor 22 (which is also one of knock event sensors 34), and the like. Other engine property measurement parameters that may be of interest, and for which additional corresponding sensors 36 may be provided, include valve travel height, vibration data, crank-cam timing, oil pressure, oil volume, coolant volume, coolant temperature, and the like. In process 54 shown in FIG. 4, measurements of the parameters sensed by these engine property sensors 36 deployed at CFR engine 20 are obtained, for example on a periodic basis during its operation, including on each of the various PRFs and test fuels. However, it may not be essential for these engine property measurement parameters to be measured exactly at the time of knock events from which octane ratings are determined, because the measurement parameters from these sensors 36 are not intended to be directed to the knock events themselves. Rather, the measurement parameters sensed by engine property sensors 36 are intended to reflect the general operational state of CFR engine 20, for example as may be related to longer term effects including engine wear.

As in the case of the environmental measurement parameters, the appropriate circuitry in sensor interface 37 executes process 55 on the engine property measurement parameters obtained in process 54, for example by digitizing the signals output by engine property sensors 36 and performing various mathematical operations on those engine property measurement data. As before, it is contemplated that these operations will typically include some type of time-averaging of the measurement parameter values from sensors 36. It is contemplated that this time-averaging and other processing of process 55 will be performed over the operational time of CRF engine 20 (i.e., maintaining time and date of the engine property measurement parameters), and need not be specifically associated with the particular fuels being run by CRF engine 20. As will be noted below, however, these times and dates can enable the engine property measurement parameters at about the times that CFR engine 20 ran the PRFs used in the octane rating determination to be associated with the other measurement parameters for those PRFs, and thus enable normalization of the octane rating for the FUE so as to account for changes in the state of the engine. In process 56, as described above, sensor interface 37 packages and transmits the engine property measurement parameter data to workstation 38, which in turn stores those data in memory in process 58.

Application of Environmental and Engine Property Measurement Parameters to the Octane Rating Determination According to certain embodiments, process 62 is executed by the appropriate processing unit in system 40 to normalize the octane number determined for the fuel under evaluation (FUE) in process 60, based on differences in one or more of these environmental measurement parameter values and engine property measurement parameters between those parameter values acquired during or at the time of the operating of CFR engine 20 on either or both of the PRFs, and those parameter values acquired during the operating of CFR engine 20 on the FUE. It is contemplated that this normalization in process 62 will not only improve the accuracy of the octane rating determination by accounting for differences in environment and engine condition at CFR engine 20 that may affect the knock event attributes (e.g., peak KI and others), but may also enable the running of the CFR engine 20 on the FUE to establish an octane rating without necessarily running the engine on the PRFs at that same time.

According to these embodiments, normalization process 62 may be performed based on either or both of one or more environmental measurement parameter values and one or more engine property measurement parameters. Accordingly, while process 62 will be described below in connection with normalization based on a set of environmental measurement parameters, it is to be understood that normalization process 62 may similarly be performed based on one or more engine property measurement parameters, either in addition to or instead of the environmental measurement parameters described below.

Figure 7:
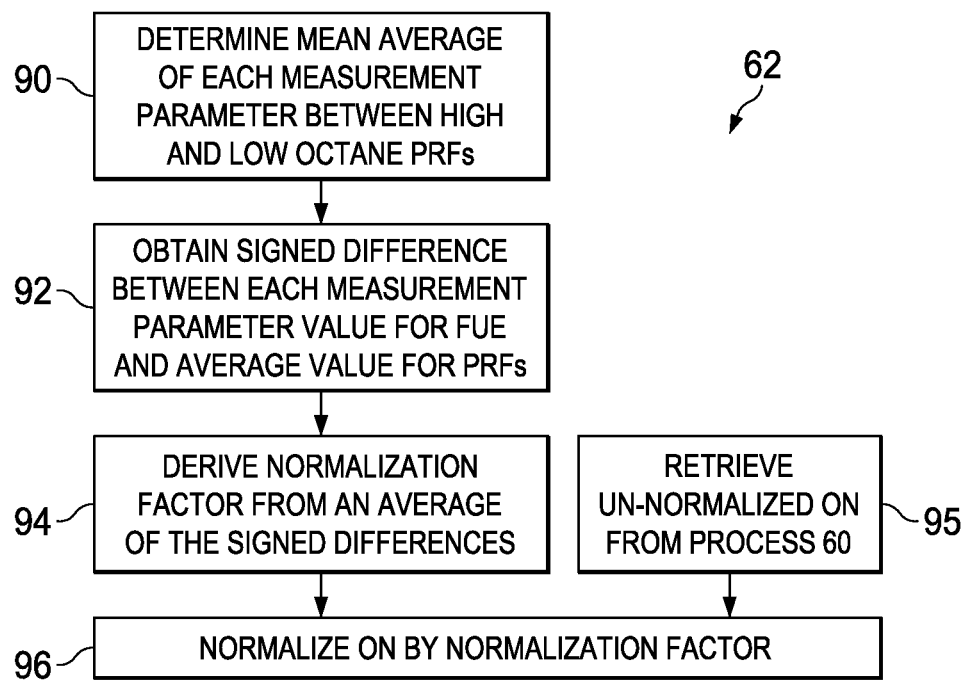
FIG. 7 is a flow diagram illustrating the operation of the method of FIG. 4 in processing environmental measurement data, according to certain embodiments.

Referring now to FIG. 7, an example of the manner in which normalization process 62 is performed according to an embodiment will now be described. This particular embodiment of normalization process 62 is well-suited for application to the octane number as determined from immediate knock events in process 60, as described above, but may also be applied to the octane number for the FUE as determined according to conventional methods, i.e., based on interpolation of the peak KI value alone.

In this embodiment, normalization process 62 begins with process 60 to obtain a mean of each time-averaged environmental measurement parameters as measured for the high octane PRF and the low octane PRF. For example, if the environmental measurement parameters of interest are:

P=barometric pressure
F=air flow
H=humidity
A=AFR (as determined from intake air flow sensor 24 and fuel flow sensor 25)
O=exhaust oxygen concentration then the determination of process 90 will result in average values $P_{ave}$, $F_{ave}$, $H_{ave}$, $A_{ave}$, $O_{ave}$ from the high octane PRF measurements ($P_H$, $F_H$, $H_H$, $A_H$, $O_H$) and low octane PRF measurements ($P_L$, $F_L$, $H_L$, $A_L$, $O_L$) as follows:

$$P_{ave} = \frac{P_H + P_L}{2}$$

$$F_{ave} = \frac{F_H + F_L}{2}$$

$$H_{ave} = \frac{H_H + H_L}{2}$$

$$A_{ave} = \frac{A_H + A_L}{2}$$

$$O_{ave} = \frac{O_H + O_L}{2}$$

Of course, additional or different environmental measurement parameters may be considered in process 90. In addition, other averaging approaches beyond a simple arithmetic may alternatively be implemented as process 90, if desired.

In process 92, signed differences between these average environmental measurement parameter values (e.g., values $P_{ave}$, $F_{ave}$, $H_{ave}$, $A_{ave}$, $O_{ave}$) and corresponding measurements obtained from environmental sensors 35 at CFR engine 20 during knock events while running the FUE are obtained. The corresponding measurements for the FUE knock events applied to process 92 may be the time-averaged measurement values from process 53, if appropriate. For the example of the environmental measurement parameters of barometric pressure, air flow, relative humidity, AFR, and exhaust oxygen concentration, process 92 will provide difference values $\pm\Delta P_{ave}$, $\pm\Delta_{ave}$, $\pm\Delta H_{ave}$, $\pm\Delta A_{ave}$, $\pm\Delta O_{ave}$ as follows:

$$\pm\Delta P = P_{ave} - P_U$$

$$\pm\Delta F = F_{ave} - F_U$$

$$\pm\Delta H = H_{ave} - H_U$$

$$\pm\Delta A = A_{ave} - A_U$$

$$\pm\Delta O = O_{ave} - O_U$$

where the values $P_U$, $F_U$, $H_U$, $A_U$, $O_U$ are the corresponding environmental measurement parameters obtained during the knock events for the FUE. Also in this process 92, the signed difference values are themselves normalized by the average environmental measurement parameter values as follows:

$$\pm P_S = \frac{\pm\Delta P}{P_{ave}}$$

$$\pm F_S = \frac{\pm\Delta F}{F_{ave}}$$

$$\pm H_S = \frac{\pm\Delta H}{H_{ave}}$$

$$\pm A_S = \frac{\pm\Delta A}{A_{ave}}$$

$$\pm O_S = \frac{\pm\Delta O}{O_{ave}}$$

These normalized difference values $\pm P_S$, $\pm F_S$, $\pm H_S$, $\pm A_S$, $\pm O_S$ are thus signed according to the sign of the difference values.

In process 94, a normalization factor is derived from these difference values obtained in process 90. According to one embodiment, this normalization factor is derived in process 94 as the arithmetic mean of the normalized difference values from process 90. For the example of the five normalized difference values $\pm P_S$, $\pm F_S$, $\pm H_S$, $\pm A_S$, $\pm O_S$ described above, normalization factor $\pm S$ is determined as:

$$\pm S = \frac{\pm P_S \pm F_S \pm H_S \pm A_S \pm O_S}{5}$$

Of course, this normalization factor may be determined by other approaches.

In process 96, the normalization factor determined in process 94 is applied to the un-normalized octane number determined for the FUE. In the example in which an octane number is determined in process 60 from attributes of knock events as described above, that octane number is retrieved from memory in process 95, and applied to normalization process 96. According to an embodiment, normalization of a previously interpolated octane rating is performed in process 96 by way of a relatively simple calculation:

$$ON_{final} = ON \times (1 \pm S)$$

where ON is the previously determined octane rating for the FUE.

As noted above, normalization process 62 may similarly be performed to normalize the octane number determined for the fuel under evaluation (FUE) in process 60 for differences in engine property measurement parameter values between those for the operating of CFR engine 20 on either or both of the PRFs, and those for the operating of CFR engine 20 on the FUE, either in addition to or instead of the set of environmental measurement parameters described above relative to FIG. 7. For example, if the octane measurements from one or more of the PRFs were obtained at a much earlier time than that at which the FUE is run, it is possible that the condition of CFR engine 20 has changed in a way that may impact the relative octane numbers. If so, normalization process 62 can also account for these differences in the operational condition of CFR engine 20, to allow determination of an accurate octane rating on the FUE without necessarily running the engine on the PRFs at that same time. In that case, these engine property measurement parameter values may not strictly be associated with the individual runs of the PRFs (or the FUE for that matter), but may be more generally associated with date and time at which CFR engine 20 was run on those particular fuels.

In the alternative to the linear normalization approach described above relative to FIG. 7, process 62 may be performed by deriving one or more normalization expressions for the effect of one or more of the environmental measurement parameters or engine property measurement parameters on octane number, as determined by the results as obtained for previous runs of PRFs and also test fuels. To the extent that the effect of variations in these environmental measurement parameters are not correlated with one another, normalization expressions for the individual measurement parameters may be successively applied in this process 62 to the octane rating determined from knock intensity or other knock event attributes in process 60. Further in the alternative, particularly for the case in which process 60 is performed using a multi-variable expression of octane rating based on knock event attributes, process 62 may be performed by numerically or statistically deriving a multi-variable normalization expression, from which an adjustment to the octane rating determined from knock intensity or other knock event attributes in process 60 is applied, based on the particular environmental measurement parameter values obtained and processed by environmental sensors 35 in process 52, or the particular engine property measurement parameter values obtained and processed by engine property sensors 36 in process 54, or both. It is contemplated that these and other approaches to incorporating the environmental and engine property measurement parameters into the octane rating determination will be apparent to those skilled in the art having reference to this specification, and that such other approaches are also within the scope of these embodiments as described and claimed.

Further in the alternative, as shown in FIG. 4, process 64 may be executed by the appropriate processing unit in system 40 to calculate a weighted octane number for the FUE from the combined datasets stored in memory in process 58, those datasets including a plurality of measurement parameter values that may include knock event measurement parameters acquired in process 50, environmental measurement parameters acquired in process 52, and engine property measurements acquired in process 54. According to this embodiment, and similarly as described above in connection with process 60, numerical processing is performed by system 40 on the available measurement parameter values to derive a multi-variable expression for octane number as a function of these measurement parameter values. The measurement parameter values for which this multi-variable expression is derived include at least the peak KI and any other knock event measurement parameters, and any environmental and engine property measurement parameter values, that are associated with running of the engine on the PRFs of known octane rating. It is contemplated that any one of a number of conventional statistical and numerical techniques may be used to derive such a multi-variable expression, including conventional analysis of variance (ANOVA) techniques; other statistical approaches; so-called "fuzzy logic" algorithms; adaptive network algorithms, and other "artificial intelligence" techniques. The result of this processing is contemplated to be an expression, whether in an explicit form or embedded in logic circuitry or other algorithms, relating the measurement parameter values for the PRFs to their known octane numbers.

In addition, the derivation of this multi-variable expression for octane number based on these measurement parameters may also include values previously acquired from the evaluation of FUEs over time in combination with their octane ratings as determined by normalization process 62.

Once such a multi-variable expression is derived, process 64 then applies the various measurement parameter values acquired for the current FUE, as run on CFR engine 20, to that multivariable expression to calculate the octane number for that FUE. As a result, the octane rating can be determined for a fuel without the need to also run CFR engine 20 on PRFs at that same time to obtain a comparison. Even if the conditions at which the PRFs were previously run differ from the current conditions at which the FUE is run, and even if the condition of CFR engine 20 itself has deteriorated or otherwise changed since the time of the PRF runs, it is contemplated that these differences can be taken into account by the multi-variable expression, given the relevant measurement parameter inputs, with little if any loss of accuracy.

According to this embodiment, the results of process 64 for the FUE may be applied as feedback to update the multi-variable expression used to calculate the octane rating. This updating with actual results, if performed over time and an appropriate number of instances, can result in a database of octane rating versus the relevant measurement parameters. Additional data as stored in this updated database can improve the statistical confidence and accuracy of the multi-variable expression, and thus the octane ratings as determined. In this regard, it is contemplated that the resulting database and the updated statistical or numerical relationships can provide greatly improved accuracy in the octane rating determination, reducing the need to frequently run CFR engine on PRFs as is required for conventional methods.

Engine Maintenance Monitoring

As described above, in some embodiments, measurement parameters are sensed by engine property sensors 36 at and acquired in process 54, for example on a periodic basis during the operation of CFR engine 20, including on each of the various PRFs and test fuels. According to an embodiment, additional processing is carried out by system 40 on those engine property data to monitor the operating condition of CFR engine 20, by way of engine property measurement parameter evaluation process 66 of FIG. 4. According to this embodiment, conventional statistical or other numerical processing operations are applied to these engine property measurement parameters acquired from CFR engine 20 in this evaluation process 66, to determine the current state of CFR engine 20. For example, process 66 may evaluate each set of engine property measurement parameters as communicated from engine property sensors 36 via sensor interface 37 to detect values that are outside of predetermined tolerances or limits. Process 66 may alternatively, or additionally, evaluate these measurement parameter values over time, using conventional statistical algorithms, to detect trends in those parameters. According to these embodiments, the results of process 66 can be reported by system 40 to the appropriate personnel in process 67, for example in the form of periodic or on-demand maintenance reports. In addition or in the alternative, upon system 40 detecting one or more unfavorable measurements or trends in engine property measurement parameters, system 40 can issue a maintenance alarm to those personnel, also in process 67.

In Conclusion

According to one or more embodiments described herein, a system and method of determining the octane rating of a fuel in a test engine is determined from a greater breadth of sensor data than in conventional test engines, which rely upon the single indication of the peak knock intensity. This greater breadth of sensor data can include various types of measurements at the test engine, including additional attributes of the knock events themselves that better describe the immediate knock event and thus can provide improved insight into the performance of various fuels, from which an octane rating can be determined with greater accuracy. In addition, some embodiments include measurements pertaining to the external engine and environmental conditions that, in combination with conventional peak knock intensities or with the additional attributes of the immediate knock events, can normalize or otherwise account for variations in those conditions that may affect the octane rating determinations. As a result, it is contemplated that improved accuracy and precision in the octane rating determination can be attained, which in turn can improve the ability of refiners and distributers to accurately blend fuels to the target octane ratings, resulting in significant economic benefit.

While one or more embodiments have been described in this specification, it is contemplated that modifications of, and alternatives to, these embodiments, such modifications and alternatives capable of obtaining one or more the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A method of determining the octane rating of a fuel, comprising the steps of:
   running a test engine on the fuel under conditions that cause the engine to knock;
   during the running step, sensing a time-varying signal from at least one knock event sensor at the engine by measuring a plurality of values over a time period including at least one knock event;
   analyzing the time-varying signal to determine measures of at least two waveform attributes of the time-varying signal and corresponding to the fuel; and
   numerically processing the measures of at least two waveform attributes, according to relationships of the measures to known measures for a same at least two waveform attributes of a reference octane fuel, to determine the octane rating of the fuel.

2. The method of claim 1, further comprising:
   during the running step, modulating at least one control variable at the engine so as to cause the engine to knock.

3. The method of claim 1, wherein the measuring step comprises:
   measuring a plurality of values over a time period including a plurality of knock events.

4. The method of claim 1, wherein the time-varying signal comprises a first time-varying signal and further comprising sensing a second time-varying signal responsive to at least one environmental parameter
   wherein the numerically processing step comprises:
      normalizing relationships of values of waveform attributes of the second time-varying signal to known octane ratings according to the at least one environmental parameter.

5. The method of claim 4 and further comprising sensing a third time-varying single responsive to at least one engine parameter;
   and wherein the normalizing step comprises:
      normalizing the relationships of values of waveform attributes of the third time-varying signal to known octane ratings according to the at least one engine property parameter.

6. The method of claim 1, further comprising, for each of a high octane primary reference fuel and a low octane primary reference fuel:
   running a test engine on the primary reference fuel under conditions that cause the engine to knock;
   sensing a time-varying signal from at least one knock sensor at the test engine by measuring a plurality of values over a time period including at least one knock event;
   wherein the numerically processing step comprises:
      deriving a relationship between octane number and the time-varying signal based on the high octane primary reference fuel and the low octane reference fuel; and
      interpolating an octane number from the measures of at least two waveform attributes of the time-varying signal and corresponding to the fuel, relative to the relationships between that octane number and a measure of the time-varying signal of the high octane primary reference fuel and the low octane primary reference fuel; and
   determining an octane rating for the fuel from an average of the interpolated octane numbers.

7. The method of claim 1, further comprising, for each of a plurality of primary reference fuels:
   running a test engine on the primary reference fuel under conditions that cause the engine to knock;
   sensing a time-varying signal from at least one knock sensor at the test engine by measuring a plurality of values over a time period including at least one knock event;
   wherein the numerically processing step comprises:
      deriving a multivariable relationship between octane number and the time-varying signal and corresponding to the fuel and the time-varying signal for each of the plurality of primary reference fuels; and
   determining an octane rating for the fuel by applying the time-varying signal and corresponding to the fuel to the multivariable relationship.

8. The method of claim 1 wherein the at least one knock event sensor comprises a pressure sensor or a vibration sensor.

9. The method of claim 1 wherein the at least two waveform attributes are selected from a set consisting of, during a knock event occurrence period, peak waveform values, calculated waveform average, calculated waveform median, and waveform width for a portion of the knock event occurrence period.

10. A system for determining the octane rating of a fuel, comprising:
    an internal combustion test engine;
    a plurality of sensors at the test engine, comprising at least one knock event sensor;
    a processing unit for executing program instructions;
    a sensor interface, coupled to the plurality of sensors and to the processing unit;
    a memory resource, coupled to the processing unit, for storing data representative of time-varying signal measure values obtained from a plurality of sensors at a test engine; and
    program memory, coupled to the processing unit, for storing a computer program including program instructions that, when executed by the one or more processing units, causes the computer system to perform a sequence of operations comprising:
       acquiring data corresponding to a time-varying signal from the at least one knock event sensor measured during the running of the test engine on the fuel under conditions that cause the test engine to knock, the time-varying signal including a plurality of values obtained for each of at least one knock event;
       analyzing the time-varying signal to determine at least two waveform attributes corresponding to at least one knock event;
       storing, in the memory resource, data corresponding to the at least two waveform attributes; and numerically processing the data corresponding to the measurement parameters according to relationships of values of those at least two waveform attributes to comparable attributes for known octane ratings, to determine the octane rating of the fuel.

11. The system of claim 10 wherein the time-varying signal comprises a first time-varying signal, wherein the plurality of sensors further comprise at least one environmental sensor;
wherein the acquiring step further comprising acquiring data corresponding to a second time-varying signal from the at least one environmental parameter;
and further comprising:
normalizing relationships of values of waveform attributes of the second time-varying signal to comparable attributes for known octane ratings according to the at least one environmental parameter.

12. The system of claim 11, wherein the plurality of sensors further comprise at least one engine property parameter;
wherein the acquiring step further comprises acquiring data corresponding to a third time-varying signal from the at least one engine property parameter;
and wherein the normalizing comprises:
normalizing relationships of values of waveform attributes of the second time-varying signal and the third time-varying signal to known octane ratings according to comparable attributes of the at least one environmental parameter and the at least one engine property parameter.

13. The system of claim 1 wherein the time-varying signal comprises a first time-varying signal, wherein the plurality of sensors further comprise at least one engine property parameter;
wherein the acquiring step further comprises acquiring data corresponding to a second time-varying signal from the at least one engine property parameter;
and wherein the normalizing comprises:
normalizing relationships of values of waveform attributes of the second time-varying signal to known octane ratings according to comparable attributes of the at least one engine property parameter.

14. The system of claim 10 wherein the at least one knock event sensor comprises a pressure sensor or a vibration sensor.

15. The system of claim 10 wherein the at least two waveform attributes are selected from a set consisting of, during a knock event occurrence period, peak waveform values, calculated waveform average, calculated waveform median, and waveform width for a portion of the knock event occurrence period.

* * * * *